(12) United States Patent
Fleming

(10) Patent No.: US 12,256,990 B2
(45) Date of Patent: Mar. 25, 2025

(54) PROCESSING OF MULTIMODAL RETINAL IMAGES

(71) Applicant: OPTOS PLC, Dunfermline (GB)

(72) Inventor: Alan Duncan Fleming, Dunfermline (GB)

(73) Assignee: OPTOS PLC, Dunfermline (GB)

(*) Notice: Subject to any disclaimer, the term of this patent is extended or adjusted under 35 U.S.C. 154(b) by 535 days.

(21) Appl. No.: 17/702,119

(22) Filed: Mar. 23, 2022

(65) Prior Publication Data

US 2022/0304566 A1    Sep. 29, 2022

(30) Foreign Application Priority Data

Mar. 26, 2021 (EP) .................................. 21165193

(51) Int. Cl.
*A61B 3/00* (2006.01)
*A61B 3/10* (2006.01)
(Continued)

(52) U.S. Cl.
CPC .......... *A61B 3/0025* (2013.01); *A61B 3/0058* (2013.01); *A61B 3/102* (2013.01);
(Continued)

(58) Field of Classification Search
CPC ..... A61B 3/0025; A61B 3/0058; A61B 3/102; A61B 3/1225; A61B 3/12; A61B 3/14;
(Continued)

(56) References Cited

U.S. PATENT DOCUMENTS

| 2012/0075584 A1 | 3/2012 | Stetson |
| 2014/0152957 A1* | 6/2014 | Reisman ............... G06T 7/0012 351/246 |

(Continued)

FOREIGN PATENT DOCUMENTS

| JP | 2008154704 A | 7/2008 |
| JP | 2012075938 A | 4/2012 |

(Continued)

OTHER PUBLICATIONS

Schmidt-Erfurth et al., A view of the current and future role of optical coherence tomography in the management of age-related macular degeneration, Eye, 31(1), pp. 26-44 (2017).

(Continued)

*Primary Examiner* — Mohammed A Hasan
(74) *Attorney, Agent, or Firm* — FAEGRE DRINKER BIDDLE & REATH

(57) ABSTRACT

There is provided a method of processing image data defining a fundus image of a retina to include supplementary information on a designated feature in the fundus image, comprising: designating (S10) a feature in the fundus image; receiving (S20) OCT data of a C-scan of the retina; selecting (S30) a subset of the OCT data representing a volumetric image of a part of the retina at a location on the retina corresponding to a location of the designated feature in the fundus image; processing (S40) the selected subset to generate, as the supplementary information, supplementary image data indicative of a variation, along a depth direction of the retina, of a measured reflectance of the eye in the selected subset; and combining (S50) the image data with the supplementary image data, such that an image defined by the combined data provides an indication of the variation at the designated feature.

14 Claims, 14 Drawing Sheets

(51) Int. Cl.
*A61B 3/12* (2006.01)
*G06T 7/00* (2017.01)
*G06T 7/33* (2017.01)
*G06T 7/50* (2017.01)
*G06T 11/00* (2006.01)

(52) U.S. Cl.
CPC .......... *A61B 3/1225* (2013.01); *G06T 7/0012* (2013.01); *G06T 7/33* (2017.01); *G06T 7/50* (2017.01); *G06T 11/001* (2013.01); *G06T 2200/24* (2013.01); *G06T 2207/10101* (2013.01); *G06T 2207/20081* (2013.01); *G06T 2207/20104* (2013.01); *G06T 2207/20212* (2013.01); *G06T 2207/30041* (2013.01)

(58) Field of Classification Search
CPC .......... G06T 7/0012; G06T 7/33; G06T 7/50; G06T 11/001; G06T 2200/24; G06T 2207/10101; G06T 2207/20081; G06T 2207/20104; G06T 2207/20212; G06T 2207/30041; G06T 11/60; G06T 5/50; G06T 2207/10024; G06T 2207/20221; G06T 2207/20101; G06V 30/19107
USPC .......................................................... 351/206
See application file for complete search history.

(56) References Cited

U.S. PATENT DOCUMENTS

| | | | | |
|---|---|---|---|---|
| 2014/0218686 | A1* | 8/2014 | Reisman | G06T 7/0012 351/246 |
| 2016/0284103 | A1 | 9/2016 | Huang | |
| 2018/0028056 | A1* | 2/2018 | Kubota | G06T 7/12 |
| 2018/0360308 | A1* | 12/2018 | Aimi | G06T 19/20 |

FOREIGN PATENT DOCUMENTS

| | | | |
|---|---|---|---|
| JP | 2016041222 A | 3/2016 | |
| JP | 2020031873 A | 3/2020 | |

OTHER PUBLICATIONS

Zur, D, et al., OCT Biomarkers as Functional Outcome Predictors in Diabetic Macular Edema Treated with Dexamethasone Implant, American Academy of Ophthalmology, 2018, vol. 125 (2), p. 267-275 (2018).

Daruich, A., et al., Mechanisms of macular edema: Beyond the Surface, Progress in Retinal and Eye Research 63, p. 20-68 (2018).

Yoshitake, T., et al. Hyperreflective Foci in the Outer Retinal Layers as a Predictor of the Functional Efficacy of Ranibizumab for Diabetic Macular Edema, Scientific Reports 10, 873 (8 sheets) (2020). (https://doi.org/10.1038/s41598-020-57646-y).

Hsia, Y., et al., Hyperreflective foci in predicting the treatment outcome of antivascular endothelial growth factor in neovascular age-related macular degeneration, Graefe's Archive for Clinical and Experimental Ophthalmology, 258(2), pp. 273-280 (2020).

Pead, E., et al., Automated detection of age-related macular degeneration in color fundus photography: a systematic review, survey of ophthalmology, 64(4), p. 498-511.

Joshi, S. et al., A review on exudates detection methods for diabetic retinopathy, Biomedicine & Pharmacotherapy, 97, pp. 1454-1460 (2018).

Amin, J., Sharif, M. and Yasmin, M., 2016, A review on recent developments for detection of diabetic retinopathy, Hindawi Publication Corporation, Scientifica, vol. 2016, Article ID 6838976 (20 pages) (2016). (http://dx.doi.org/10.1155/2016/6838976).

European Search Report issued Sep. 21, 2021 in European Patent Application EP 21 16 5193.

Wartak Andreas et al., Multi-directional optical coherence tomography for retinal imaging, Biomedical Optics Express, vol. 8, No. 12, p. 5560 to 5578, XP055823572 (2017).

Kafieh R., et al., A Review of Algorithms for Segmentation of Optical Coherence Tomography from Retina, Journal of Medical Signals & Sensors, vol. 3, Issue I, pp. 45-60 (2013).

Optos California brochure, 2021 (4 sheets).

\* cited by examiner

PROCESSING OF MULTIMODAL RETINAL IMAGES

This application claims the benefit of priority based on European Patent Application EP 21 165 193.0 filed Mar. 26, 2021 and European Patent Application EP 21 207 444.7 filed Nov. 10, 2021, which is incorporated by reference herein in its entirety, as if set forth fully herein.

TECHNICAL FIELD

Example aspects herein generally relate to the field of retinal image processing and, more particularly, to the processing of a reflectance image of a retina to include supplementary information derived from optical coherence tomography (OCT) data acquired from the retina.

BACKGROUND

Two-dimensional images of the ocular fundus acquired by a fundus camera or a scanning laser ophthalmoscope (SLO), for example, are widely used to detect various eye diseases, as well as systemic diseases in a subject. Although these imaging methods tend to have a varying sensitivity with depth in the retina, their depth specificity tends to be low, so that the depth of an observed feature in a retinal fundus image is usually uncertain. As some common eye diseases, such as age-related macular degeneration, diabetic retinopathy and retinal vein occlusion, are associated with features such as hyper-reflective dots which furthermore have a similar appearance in retinal fundus image, it is often difficult for a clinician to distinguish between these diseases from an inspection of a retinal fundus image alone. Artefacts in retinal fundus images, such as those resulting from a highly reflective inner limiting membrane (ILM), and atrophy of the retinal pigment epithelium (RPE) may also confuse the identification of disease-related features, such as exudative, RPE-related and drusenoid hyper-reflective dots. Further information on a feature of interest that has been identified on a retinal fundus image may be obtained by examining an OCT thickness map which covers the feature of interest.

SUMMARY

There is provided, in accordance with a first example aspect herein, a computer-implemented method of processing image data defining a fundus image of a portion of a retina of an eye to include supplementary information on a designated feature in the fundus image. The method comprises designating a feature in the fundus image, receiving optical coherence tomography (OCT) data of a C-scan of the portion of the retina, and selecting a subset of the OCT data which represents a volumetric image of a part of the retina at a location on the retina corresponding to a location of the designated feature in the fundus image. The method further comprises processing the selected subset of the OCT data to generate, as the supplementary information, supplementary image data indicative of a variation, along a depth direction of the retina, of a measured reflectance of the eye in the selected subset of the OCT data. The method further comprises generating combined image data by combining the image data with the supplementary image data, such that a combined image defined by the combined image data provides an indication of the variation of the measured reflectance of the eye in the selected subset of the OCT data at the designated feature.

In the computer-implemented method according to the first example aspect, the combined image data may be generated by replacing pixel values of a subset of pixels of the fundus image data with pixel values of the supplementary image data, such that a combined image defined by the combined image data provides an indication of the variation of the measured reflectance of the eye in the selected subset of the OCT data at the designated feature. In some example embodiments, the combined image data may be generated by replacing pixel values of a subset of pixels of the fundus image data, which subset of pixels defines a subregion of the fundus image which is at the location of the designated feature in the fundus image, with pixel values of the supplementary image data, such that a combined image defined by the combined image data provides an indication of the variation of the measured reflectance of the eye in the selected subset of the OCT data at the designated feature. In some other example embodiments, the supplementary image data may define a graphic which is indicative of the variation, along the depth direction of the retina, of the measured reflectance of the eye in the selected subset of the OCT data or, more specifically, how the measured reflectance of the eye, as indicated in the selected subset of the OCT data varies along a depth direction of the retina. In these other example embodiments, the combined image data may be generated by replacing pixel values of a subset of pixels of the fundus image data with pixel values of the supplementary image data such that a combined image defined by the combined image data comprises the graphic, which is overlaid on the fundus image so as to provide an indication of the variation of the measured reflectance of the eye in the selected subset of the OCT data at the designated feature.

Additionally or alternatively, the computer-implemented method according to the first example aspect may, in accordance with an example embodiment, further comprise causing the fundus image and a cursor to be displayed on a display, such that the cursor can be controlled to move over the displayed fundus image by a signal from a user input device, wherein the feature in the fundus image is designated by recording, in response to a feature designation command, a value of a first location indicator that is indicative of a display location of the cursor on the displayed fundus image.

The method of the example embodiment may further comprise: processing the OCT data to generate an OCT en-face image of the portion of the retina; and causing the OCT en-face image to be displayed on the display together with the fundus image, such that the cursor can be controlled to move over the displayed OCT en-face image by the signal from the user input device, wherein the subset of the OCT data is selected based on a value of a second location indicator, which is indicative of a display location of the cursor when the cursor has been guided by the signal from the user input device to overlay a part of the displayed OCT en-face image which corresponds to the designated feature in the displayed fundus image.

The feature in the fundus image may alternatively be designated automatically by a feature extraction algorithm. In this case, the computer-implemented method may further comprise: causing the fundus image and a feature location indicator, which indicates a location of the designated feature in the fundus image, to be displayed on a display; processing the OCT data to generate an OCT en-face image of the portion of the retina; and causing the OCT en-face image and a cursor to be displayed on the display together with the fundus image, such that the cursor can be controlled to move over the displayed OCT en-face image by a signal from a user input device, wherein the subset of the OCT data is selected based on a value of a second location indicator, which is indicative of a display location of the cursor when the cursor has been guided by the signal from the user input device to overlay a part of the displayed OCT en-face image whose location corresponds to the location of the designated feature in the fundus image that is indicated by the feature location indicator.

Alternatively, where the feature in the fundus image is designated automatically by a feature extraction algorithm, the subset of the OCT data may be selected by applying a geometric transformation, which maps locations in the fundus image to corresponding A-scan locations in the OCT data, to the location of the feature in the fundus image which has been designated by the feature extraction algorithm.

In any of the computer-implemented methods set out above, the feature may be one of a dot and a hyper-reflective dot in the fundus image, the feature having a pathological cause or being caused by a reflection from an inner limiting membrane of the retina. For example, the feature may have a pathological cause comprising one of blood leakage, exudation, drusen, atrophy and/or naevi in the retina, and atrophy of a retinal pigment epithelium in the retina.

In the foregoing, the selected subset of the OCT data may be processed to generate the supplementary image data by the following scheme 1, scheme 2 or scheme 3.

Scheme 1:

The selected subset of the OCT data is processed to generate the supplementary image data by: detecting a plurality of anatomical layers of the eye in the selected subset of the OCT data, the anatomical layers comprising one or more retinal layers of the retina; calculating, for each of at least two of the detected anatomical layers, a respective sum value by summing values of data elements of the subset of the OCT data in the anatomical layer; calculating, for each of the at least two of the detected anatomical layers, a respective ratio between the sum value calculated for the anatomical layer and a sum of all the data elements that are in the at least two of the detected anatomical layers and in the subset of the OCT data; and generating, as the supplementary image data, and based on an ordered sequence of the calculated ratios, wherein the calculated ratios are arranged in order of the corresponding anatomical layers in the eye, colour information defining a colour which is to be displayed in the combined image and identifies the ordered sequence of the calculated ratios, such that the colour is indicative of the variation, along the depth direction of the retina, of the measured reflectance of the eye in the selected subset of the OCT data. For example, three anatomical layers in the selected subset of the OCT data may be detected, and the colour information may be generated by assigning, to each of a red colour component, a green colour component and a blue colour component of the colour to be displayed in the combined image, a respective weighting for the colour component in accordance with a respective one of the calculated ratios in the ordered sequence of the calculated ratios.

Scheme 2:

The selected subset of the OCT data is processed to generate the supplementary image data by: detecting a plurality of anatomical layers of the eye in the selected subset of the OCT data, the anatomical layers comprising one or more retinal layers of the retina; calculating, for each anatomical layer of the detected anatomical layers, a respective sum value by summing values of data elements of the subset of the OCT data in the anatomical layer; selecting, based on the calculated sum values, an anatomical layer of the detected anatomical layers which provides a dominant contribution to the measured reflectance of the eye; and generating, as the supplementary image data, graphic image data defining a graphic which identifies the selected anatomical layer.

Scheme 3:

The selected subset of the OCT data represents a volumetric image of a part of the retina having a feature of a predetermined type and is processed to generate the supplementary image data by: training a model for determining a depth of the feature of the predetermined type in the depth direction of the retina, by supervised learning of examples of OCT data of pathological regions of at least one other retina, each of the examples of OCT data comprising a single OCT A-scan or two or more adjacent OCT A-scans, and each of the pathological regions having a respective feature of the predetermined type, wherein an indication of a respective depth of the respective feature in the depth direction of the retina in each of the examples of OCT data is specified by a user during the training; processing the selected subset of the OCT data using the trained model to determine the depth of the feature in the depth direction of the retina; and generating, as the supplementary image data, one of (i) graphic image data defining a graphic which indicates the determined depth of the feature and is to be overlaid on the fundus image (10) so as to indicate a location of the feature in the combined image (40), and (ii) colour information defining a colour which is to be displayed at a location of the feature in the combined image and indicates the determined depth of the feature.

There is also provided, in accordance with a second example aspect herein, a computer program comprising computer program instructions which, when executed by a computer, cause the computer to perform the method set out above. The computer program may be stored on a non-transitory computer-readable storage medium, or it may be carried by a signal.

There is also provided, in accordance with a third example aspect herein, an apparatus for processing image data defining a fundus image of a portion of a retina of an eye to include supplementary information on a designated feature in the fundus image. The apparatus comprises a feature designation module arranged to designate a feature in the fundus image, and a receiver module arranged to receive OCT data of a C-scan of the portion of the retina. The apparatus further comprises a selection module arranged to select a subset of the OCT data which represents a volumetric image of a part of the retina at a location on the retina corresponding to a location of the designated feature in the fundus image, and a supplementary image data generation module arranged to process the selected subset of the OCT data to generate, as the supplementary information, supplementary image data indicative of a variation, along a depth direction of the retina, of a measured reflectance of the eye in the selected subset of the OCT data. The apparatus further comprises a combined image data generation module arranged to generate combined image data by combining the image data with the supplementary image data, such that a combined image defined by the combined image data provides an indication of the variation at the designated feature.

In the apparatus according to the third example aspect, the combined image data generation module may be arranged to generate the combined image data by replacing pixel values of a subset of pixels of the fundus image data with pixel values of the supplementary image data, such that a combined image defined by the combined image data provides an indication of the variation of the measured reflectance of the eye in the selected subset of the OCT data at the designated feature. In some example embodiments, the combined image data generation module may be arranged to generate the combined image data by replacing pixel values of a subset of pixels of the fundus image data, which subset of pixels defines a subregion of the fundus image which is at the location of the designated feature in the fundus image, with pixel values of the supplementary image data, such that a combined image defined by the combined image data provides an indication of the variation of the measured reflectance of the eye in the selected subset of the OCT data at the designated feature. In some other example embodiments, the supplementary image data generation module may be arranged to generate supplementary image data which defines a graphic indicative of the variation, along the depth direction of the retina, of the measured reflectance of the eye in the selected subset of the OCT data or, more specifically, how the measured reflectance of the eye, as indicated in the selected subset of the OCT data varies along a depth direction of the retina. In these other example embodiments, the combined image data generation module may be arranged to generate the combined image data by replacing pixel values of a subset of pixels of the fundus image data with pixel values of the supplementary image data such that a combined image defined by the combined image data comprises the graphic, which is overlaid on the fundus image so as to provide an indication of the variation of the measured reflectance of the eye in the selected subset of the OCT data at the designated feature.

BRIEF DESCRIPTION OF THE DRAWINGS

Example embodiments will now be explained in detail, by way of non-limiting example only, with reference to the accompanying figures described below. Like reference numerals appearing in different ones of the figures can denote identical or functionally similar elements, unless indicated otherwise.

DETAILED DESCRIPTION OF EXAMPLE EMBODIMENTS

There are described in the following a method, apparatus and computer program for processing retinal fundus image data that may assist a clinician to assess a distribution of, and distinguish between, features of some common eye diseases which have similar appearance in retinal fundus images, such as diabetic retinopathy, age-related macular degeneration and retinal vein occlusion, and that may help avoid misreading of retinal fundus images caused by specular imaging artefacts. The techniques described herein may allow additional information in OCT data to be leveraged for a clearer rendering of features (e.g. bright spots) in the retinal fundus images. In some example embodiments, the information can be assimilated by the user without reviewing OCT data. Furthermore, in some example embodiments, the user may be notified of whether a feature in a retinal fundus image is coincident with a feature in OCT, thereby helping to avoid misinterpretation of artefactual spots and the like in the retinal fundus image.

Example embodiments herein will now be described in more detail with reference to the accompanying drawings.

First Example Embodiment

Figure 1:
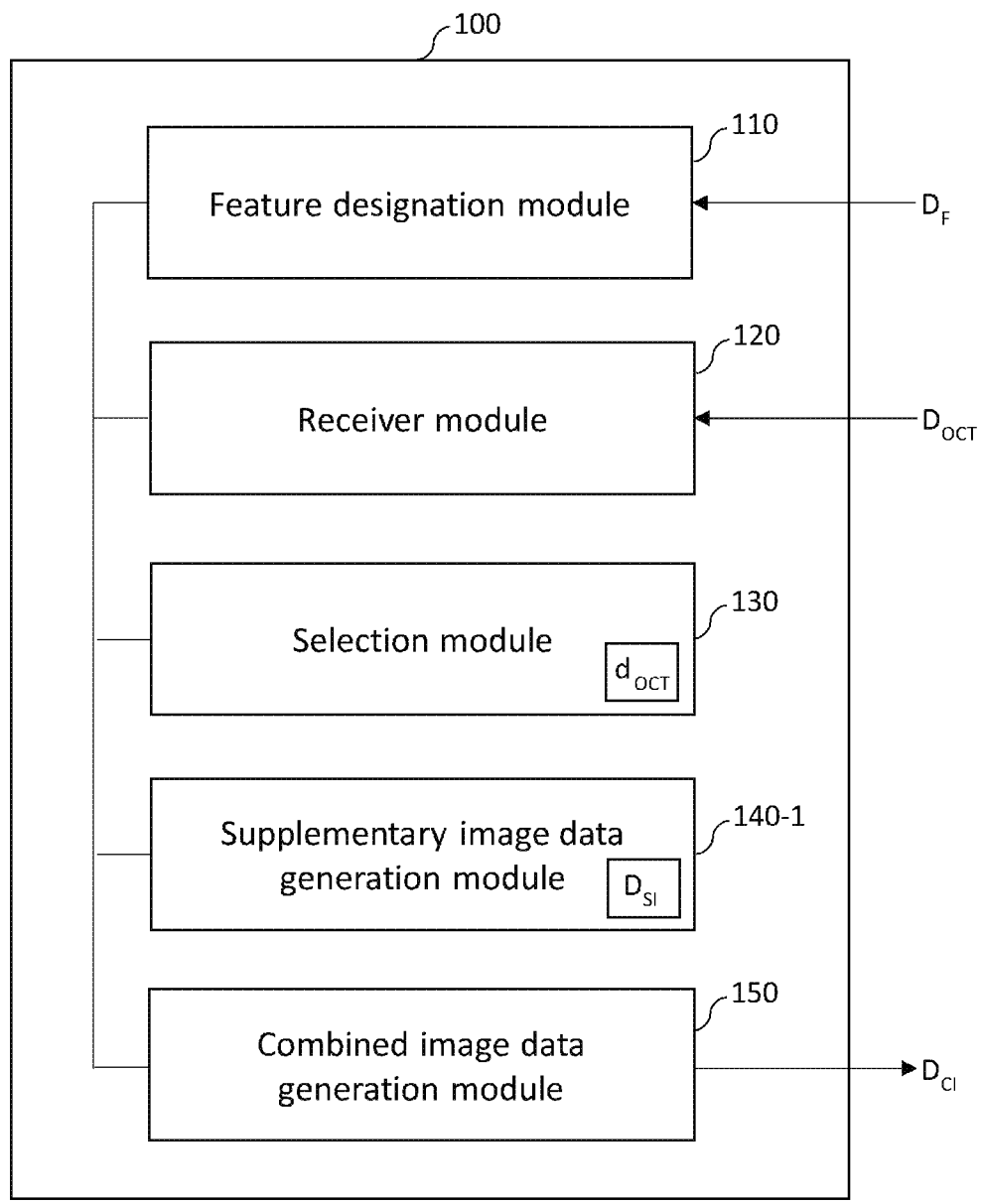
FIG. 1 is a schematic illustration of an apparatus for processing image data, according to a first example embodiment.
Figure 2:
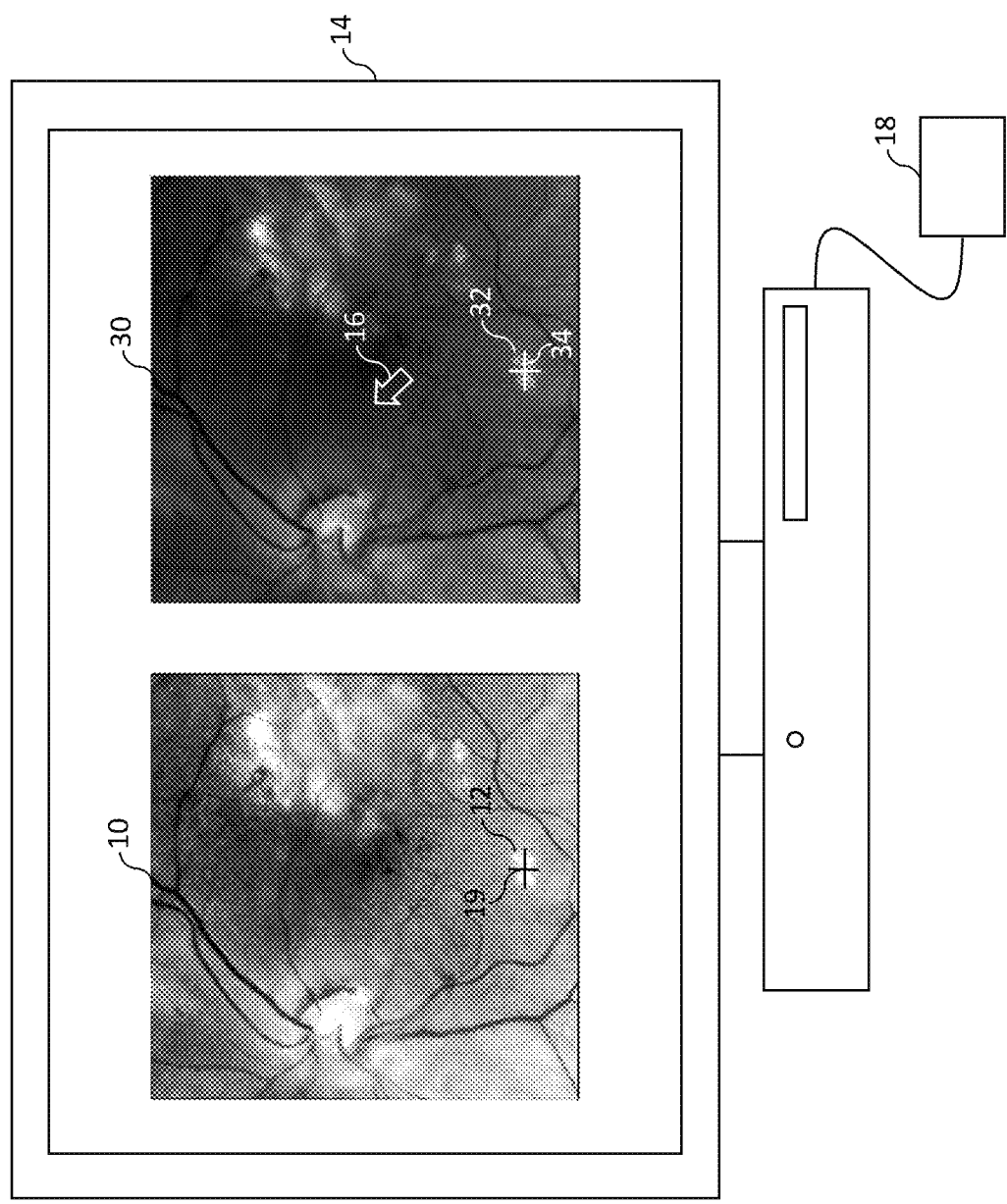
FIG. 2 is a schematic illustration of a display displaying a fundus image and an en-face OCT image in first example embodiment.

FIG. 1 is a schematic illustration of an apparatus 100 for processing image data according to a first example embodiment. As will be described in more detail below, the apparatus 100 is arranged to process received image data $D_F$, which defines a fundus image 10 of a portion of a retina of an eye, to include supplementary information on a designated feature 12 in the fundus image 10, as illustrated in FIG. 2, where the fundus image 10 and the designated feature 12 are shown to be displayed on a display 14 (e.g. a visual display unit, such as a computer monitor), together with a user-controlled cursor 16.

The fundus image of the retina (also referred to herein as a retinal fundus image) 10 may be acquired by any fundus imaging process by which a two-dimensional representation of the three-dimensional (semi-transparent) retinal tissues projected onto an imaging plane of a fundus imaging apparatus (not shown) is obtained using light collected from the retina. The fundus image may be acquired by illumination of the retina by global illumination or by a scanned light beam provided by the fundus imaging apparatus. The light reflected from the retina is collected by a receiver of the fundus imaging apparatus, and its position-dependent intensity is detected, and then converted into the image data $D_F$ representing the two-dimensional fundus image 10. Thus, the term 'fundus imaging' used herein refers to any process which results in a two-dimensional image of a portion of the retina, wherein image pixel values represent respective intensities of light collected from the retina, and is to be contrasted with OCT imaging (discussed below).

The fundus image 10 may be acquired by one of many types of fundus imaging apparatus known to those versed in the art, including but not limited to fundus cameras and scanning laser ophthalmoscopes (SLOs). In combination with light filters, these types of fundus imaging apparatus may be used to acquire monochromatic or autofluorescence images of the fundus and, with the injection of intravenous contrast material, may also be used to acquire fundus fluorescein angiograms, indocyanine green angiograms and the like. Fundus imaging thus covers various modalities/techniques, including monochromatic fundus photography, colour fundus photography, scanning laser ophthalmoscopy (SLO), adaptive optics SLO, fluorescein angiography and indocyanine angiography.

The fundus imaging apparatus may have a relatively narrow field of view or 30°-55° or so that is typical in conventional fundus imaging, or it may be a widefield fundus imaging apparatus having a field of view of about 100°. As a further alternative, the fundus imaging apparatus may be an ultra-widefield (UWF™) fundus imaging apparatus having a field of view of about 200°, such as the Optos California™ system made by Optos plc.

As shown in FIG. 1, the apparatus 100 comprises a feature designation module 110, which is arranged to designate a feature 12 in the fundus image 10 received from the fundus imaging apparatus. The feature 12 may be an image of a structure having a relatively high reflectivity (whether inside the retina or in another part of the eye being imaged), and may therefore be a part of the fundus image 10 representing higher reflectance than a region of the fundus image 10 surrounding that part. The feature 12 may alternatively be an image of a structure having a relatively low reflectivity (whether inside the retina or in another part of the eye being imaged), and may therefore be a part of the fundus image 10 representing lower reflectance than a region of the fundus image 10 surrounding that part. Although the description of the apparatus 100 is described herein by reference to a single designated feature 12 for convenience, it will be appreciated that multiple features in the fundus image 10 may be designated, and the operations described in the following may be performed on the basis of each of these designated features.

The feature 12 may, for example, be a dot feature, whose extent in the fundus image is small compared to the size of the fundus image. Dot features of this kind can have a pathological cause, such as blood leakage, exudation, drusen, atrophy and/or naevi in the retina. Dot features related to these pathologies have a very similar, characteristic appearance (in terms of their sizes and the brightness difference between dot features and their surroundings in the fundus image 10), and are difficult for a clinician to disambiguate by inspection of the fundus image 10 alone. They are also difficult to disambiguate from dot features having non-pathological causes, such as floaters in the ocular vitreous, reflex from retinal surfaces such as the inner limiting membrane, or reflections from imperfections such as dust in the imaging system, for example, which have a similar appearance in fundus images to the aforementioned pathological dot features.

The dot feature may be a hyper-reflective dot/focus, for example, which is often observed in retinal fundus images. Hyper-reflective foci may have a pathological cause such as blood leakage, exudation, drusen, atrophy and/or naevi in the retina or atrophy of a retinal pigment epithelium in the retina, or a non-pathological cause such as a reflection from an inner limiting membrane of the retina. Hyper-reflective dots in all these cases have a very similar, characteristic appearance, and are difficult to distinguish by inspection of the fundus image 10 alone.

The feature designation module 110 may designate the feature 12 in the fundus image 10 in one of a number of different ways. For example, in the present example embodiment, the feature designation module 110 causes the fundus image 10 and the cursor 16 to be displayed on the display 14. The display location of the cursor 16 on the displayed fundus image 10 is controllable by a signal from a user input device 18, such as a computer mouse, a trackpad or the like. In the present example embodiment, the feature 12 in the fundus image 10 is designated by recording, in response to a feature designation command, a value of a first location indicator that is indicative of a display location of the cursor 16 when the cursor has been guided by the signal to overlay the displayed fundus image 10. The feature designation module 110 may cause a graphic 19 to be overlaid on the reluctance image 10 at the location in the fundus image 10 indicated by the first location indicator.

The feature designation command may, as in the present example embodiment, be provided by the user, for example by the user operating the user input device 18 (e.g. providing a mouse click in case the user input device is provided in the form of a computer mouse, or a finger tap in case the user input device is provided in the form of a trackpad). The feature designation command may alternatively be provided by the user operating another user input device, for example pressing a key on a computer keyboard. As a further alternative, the feature designation command may be generated by the feature designation module 110 in response to a prescribed condition being met, for example the expiry of a predetermined time period which is started by a display on the display 14 of an instruction to the user to designate a feature of interest in the displayed fundus image 10.

The feature designation module 110 need not rely on such a human interaction to designate the feature 12, and may, in an alternative example embodiment, perform the designation automatically, using one of a number of feature extraction algorithms known to those versed in the art, for example as described in "Automated detection of age-related macular degeneration in color fundus photography: a systematic review" by Pead, E., Megaw, R., Cameron, J., Fleming, A., Dhillon, B., Trucco, E. and MacGillivray, T., 2019, published in *Survey of Ophthalmology*, 64(4), 2019 at pages 498-511, or "A review on exudates detection methods for diabetic retinopathy" by Joshi, S. and Karule, P. T., published in *Biomedicine & Pharmacotherapy*, 97, 2018, at pages 1454-1460, or "A review on recent developments for detection of diabetic retinopathy" by Amin, J., Sharif, M. and Yasmin, M., *Scientifica*, 2016.

Figure 3:
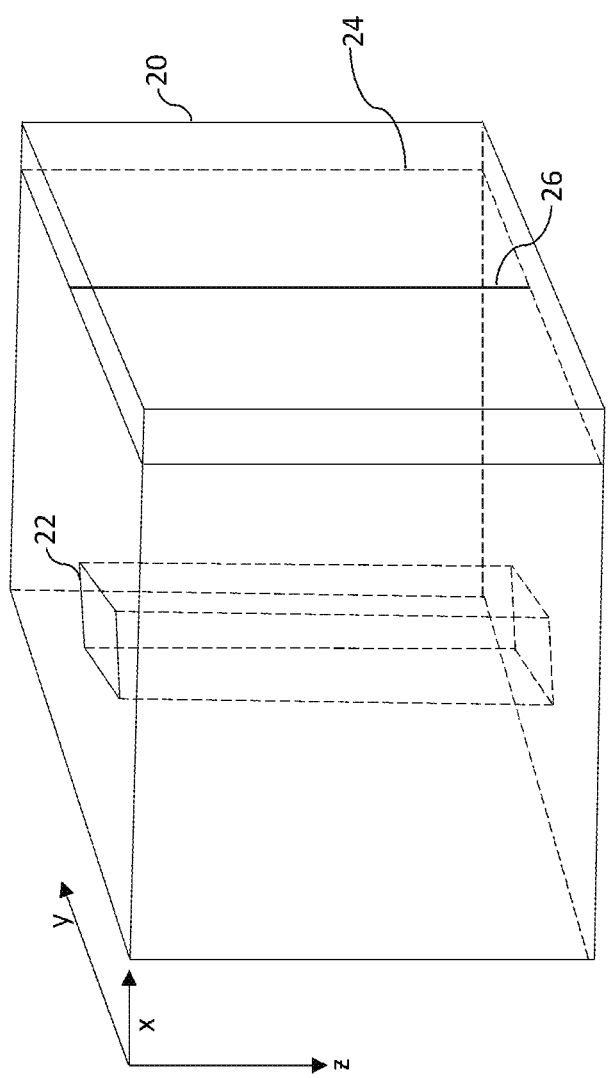
FIG. 3 is a schematic illustration OCT data and a subset thereof which is selected by the selection module of the first example embodiment.

The apparatus 100 also has a receiver module 120, which is arranged to receive optical OCT data $D_{OCT}$ of a C-scan (shown at 20 in FIG. 3) of the portion of the retina acquire by an OCT imaging system (not shown). The apparatus 100 also has a selection module 130, which is arranged to select a subset $d_{OCT}$ of the OCT data $D_{OCT}$, which represents a volumetric image (defined by voxels of a set 22 of A-scans in FIG. 3) of a part of the retina at a location on the retina corresponding to a location of the designated feature 12 in the fundus image 10. As illustrated schematically in FIG. 3, the C-scan 20 is composed of a series of B-scans 24, wherein each B-scan 24 is composed of a series of A-scans 26. The value of each data element in an A-scan 26 provides an indication of a measured reflectance of the eye at a respective location in the depth direction of the retina that corresponds to the location of the data element along the A-scan 26 (i.e. along the z-axis direction in FIG. 3). The location of the A-scan 26 along the y-axis and x-axis directions of data element array forming the C-scan 20 corresponds to a location on the retina of a measurement taken by the OCT imaging system to acquire the A-scan 26.

The OCT imaging system used to acquire the OCT data $D_{OCT}$ may be of any type known to those versed in the art, for example a point-scan OCT imaging system, which can acquire an OCT image by scanning a laser beam laterally across a region of the eye. The OCT imaging system may alternatively be a parallel acquisition OCT imaging system, such as Full-Field OCT (FF-OCT) or Line-Field OCT (LF-OCT), which may offer superior A-scan acquisition rates (up to tens of MHz) by illuminating an area or a line on the sample, rather than scanning a single spot across the eye. In FF-OCT, a two-dimensional region of the eye is illuminated at the same time and the lateral positions across the region are concurrently captured using a photodetector array such as a high-speed charge-coupled device (CCD) camera. Where the OCT imaging system is a Full-field OCT, it may take the form of a full-field time-domain OCT (FF-TD-OCT) or full-field swept-source OCT (FF-SS-OCT), for example. In FF-TD-OCT, the optical length of the reference arm can be varied during a scan in order to image regions at different depths in the eye. Each frame captured by the high-speed camera in FF-TD-OCT therefore corresponds to a slice of the eye at a respective depth within the eye. In FF-SS-OCT, the sample region is full-field illuminated using a swept light source that emits light whose wavelength varies over time. As the wavelength of the swept light source is swept over a range of optical wavelengths, a spectrogram correlating reflectivity information against optical wavelength can be generated by the high-speed camera for each camera pixel. Each frame captured by the camera therefore corresponds to reflectivity information for a single wavelength of the swept light source. Upon acquiring a frame for every wavelength of the swept light source, a C-scan of the region can be obtained by performing a Fourier transform on the samples of spectrograms generated by the camera. In line-field OCT (LF-OCT), a line of illumination may be provided to the sample and a B-scan may be acquired in the imaging process. Line-field OCT may be classified as line-field time-domain OCT (LF-TD-OCT), line-field swept-source OCT (LF-SS-OCT), or line-field spectral-domain OCT (LF-SD-OCT), for example.

The OCT imaging system used to acquire the OCT data and the fundus imaging apparatus used to acquire the fundus image may be separate devices. It should be noted, however, that the fundus image and the OCT data may be acquired by a single, multimodal retinal imaging system, such as the Silverstone combined UWF retinal imaging device and UWF-guided swept source OCT scanner made by Optos plc.

The subset $d_{OCT}$ of the received OCT data $D_{OCT}$ may, as in the present example embodiment, be selected by the selection module 130 based on an input from a user who has inspected a two-dimensional representation of the OCT data $D_{OCT}$ shown on the display 14, determined a location in the representation of the OCT data $D_{OCT}$ which corresponds to the location of the designated feature 12 in the reference image 10 also shown on the display 14, and guided the cursor 16 to overlay the determined location in the representation of the OCT data $D_{OCT}$.

More particularly, in the present example embodiment, the selection module 130 processes the received OCT data $D_{OCT}$ to generate an OCT en-face image of the portion of the retina. The OCT en-face image 30 is a projection of the (three-dimensional) C-scan 20 image to the same two-dimensional plane that would be viewed in the fundus image 10 of the same portion of the retina. The generation of the OCT en-face image 30 may involve a summation, a weighted summation or a maximisation of the data elements (voxels) of the C-scan along the depth axis (z) of the OCT C-scan 20.

The selection module 130 causes the OCT en-face image 30 to be displayed on the display 14 together with the fundus image 10, for example alongside the fundus image 10 as illustrated in FIG. 2, with the cursor 16 being controllable by the signal from the user input device 18 to move over the displayed OCT en-face image 30. Although the display 14 is provided in the form of a single visual display unit in the present example embodiment, the display 14 may alternatively be provided in the form of a first monitor (or other visual display unit) and a second monitor (or other visual display unit, not necessarily of the same kind as the first visual display unit), which are arranged to respectively display the fundus image 10 and the OCT en-face image 30 simultaneously to the user.

In the present example embodiment, the subset $d_{OCT}$ of the OCT data $D_{OCT}$ is selected by the selection module 130 based on a value of a second location indicator that is indicative of a display location of the cursor 16 when the cursor 16 has been guided by the signal from the user input device 18 to overlay a part 32 of the displayed OCT en-face image 30 which is judged by the user (based on a comparison of retinal features in the displayed images 10 and 30) to correspond to the designated feature 12 in the displayed fundus image 10, and in response to a feature designation command of the kind described above. The subset $d_{OCT}$ of the OCT data $D_{OCT}$ may be selected based on the value of a second location indicator by mapping the value of the second location indicator to an A-scan of the OCT C-scan 20 having a corresponding (x, y) coordinate, and selecting the A-scan, or the A-scan together with a predefined arrangement of neighbouring (adjacent) A-scans (e.g. m adjacent A-scans that are nearest to the mapped to- and selected A-scan in the x-y plane of the C-scan 20, where m is an integer, preferably greater than 4 and more preferably greater than 8), as the subset $d_{OCT}$ of the OCT data $D_{OCT}$.

It should be noted, however, that the subset $d_{OCT}$ of the OCT data $D_{OCT}$ need not be defined by the mapped to- and selected A-scan together with a predefined arrangement of neighbouring A-scans but may alternatively be defined by a set of A-scans that are enclosed by a contour in the x-y plane of the C-scan 20 defined by straight-line segments linking A-scans of the C-scan 20 that have been selected based on respective values of the second location indicator, in response to the user issuing multiple feature designation commands as he/she moves the cursor 16 around the boundary of a feature of interest in the fundus image 10. The subset $d_{OCT}$ of the OCT data $D_{OCT}$ may therefore correspond to a region of the OCT en-face image 30 having a predefined shape (as in the present example embodiment) or a shaped defined by the user.

The selection module 130 may cause a graphic 34 to be overlaid on the OCT en-face image 30 at the location in the en-face image 30 indicated by the second location indicator. The graphic 34 may the same as the graphic 19, or different from graphic 19 in case a different colour and/or shape for the graphic 34 provides better visibility on the OCT en-face image 30, for example. Similarly, the appearance of the cursor 16 whilst overlaying the displayed fundus image 10 may be different (in terms of shape and/or colour) from its appearance whilst overlaying the displayed OCT en-face image 30.

In the alternative example embodiment identified above, in which the feature designation module 110 designates the feature 12 in the fundus image 10 automatically by use of a feature extraction algorithm, the selection module 130 may cause a feature location indicator (e.g. in the form of graphic 19) to be overlaid on the displayed fundus image 10, so as to indicate the location of the designated feature 12 in the fundus image 10. In this case, the subset $d_{OCT}$ of the OCT data $D_{OCT}$ may be selected based on a value of the second location indicator as described above, which is indicative of a display location of the cursor 16 when the cursor 16 has been guided by the signal from the user input device 18 to overlay a part of the displayed OCT en-face image 30 whose location is judged by the user (based on a comparison of retinal features in the displayed images 10 and 30) to correspond to the location in the fundus image 10 indicated by the feature location indicator.

It should be noted, however, that the correspondence between the location of the designated feature 12 in the fundus image 10 and the location of the subset door within OCT data $D_{OCT}$ need not be determined by a user from an inspection of a displayed fundus image 10 and a displayed OCT en-face image of a common portion of the retina. In some example embodiments, the location of the subset $d_{OCT}$ within OCT data $D_{OCT}$ may be determined automatically, on the basis of the location of the designated feature 12 in the fundus image 10, by use of a predetermined geometric transformation. The predetermined geometric transformation maps locations in the fundus image 10 to corresponding A-scan locations in the OCT data, and may be applied by the selection module 130 to the location of the feature 12 in the fundus image 10 that has been designated by the feature extraction algorithm, in order to identify a corresponding A-scan location in the C-scan 20 of an A-scan 26 which is to be included in the subset $d_{OCT}$ of the OCT data (optionally, together with one or more adjacent A-scans in the C-scan 20).

The geometric transformation may be determined in one of a number of different ways. For example, the geometric transformation may be determined by registering image data $D_F$ defining the fundus image 10 with image data defining an OCT en-face image 30 that has been generated as described above, without the OCT en-face image 30 being displayed to the user. Any intensity- and/or feature-based registration algorithm know to those versed in the art may be used to determine the geometric transformation and thus establish a point-to-point correspondence between locations in the fundus image 10 and lateral positions (defined by coordinates along the x- and y-axes in FIG. 3) in the OCT C-scan 20. It should be noted that such registration algorithms may operate directly on the two-dimensional dataset defining the fundus image 10 and the three-dimensional dataset defining the OCT C-scan 20, rather than on the two-dimensional dataset defining the fundus image 10 and the two-dimensional dataset of the OCT en-face image 30 that is derived from the three-dimensional dataset of the OCT C-scan 20.

In some example embodiments, both the designation of a feature in the fundus image 10 by the feature designation module 110, and the selection of the subset $d_{OCT}$ of the OCT data $D_{OCT}$ by the selection module 130, may be performed automatically (i.e. without any user input). Thus, in such example embodiments, the feature designation module 110 may designate a part of the image data $D_F$ defining a feature 12 in the fundus image 10 using a feature extraction algorithm, and the selection module 130 may select the subset $d_{OCT}$ of the OCT data $D_{OCT}$ by applying the geometric transformation described above to the location of the designated part in the image data $D_F$ of the fundus image 10. In these example embodiments, the designation of the feature 12 and the selection of the subset $d_{OCT}$ of the OCT data is performed without displaying any representation of the image data $D_F$ of the fundus image 10 or of the OCT data $D_{OCT}$ to the user, and without requiring any user input.

Referring again to FIG. 1, the apparatus 100 also has a supplementary image data generation module 140-1, which is arranged to process the selected subset $d_{OCT}$ of the OCT data $D_{OCT}$ to generate, as the supplementary information, supplementary image data $D_{SI}$ indicative of a variation, along the depth direction of the retina (i.e. the direction in which light rays enter the retina), of a measured reflectance of the eye in the selected subset $d_{OCT}$ of the OCT data. The apparatus 100 also has a combined image data generation module 150, which is arranged to generate combined image data $D_{CI}$ by combining the image data $D_F$ with the supplementary image data $D_{SI}$, such that a combined image defined by the combined image data $D_{CI}$ provides an indication of the variation of the measured reflectance of the eye in the selected subset $d_{OCT}$ of the OCT data $D_{OCT}$ at the designated feature. The functionality of the supplementary image data generation module 140-1 and the combined image data generation module 150 is described in more detail below.

Figure 4:
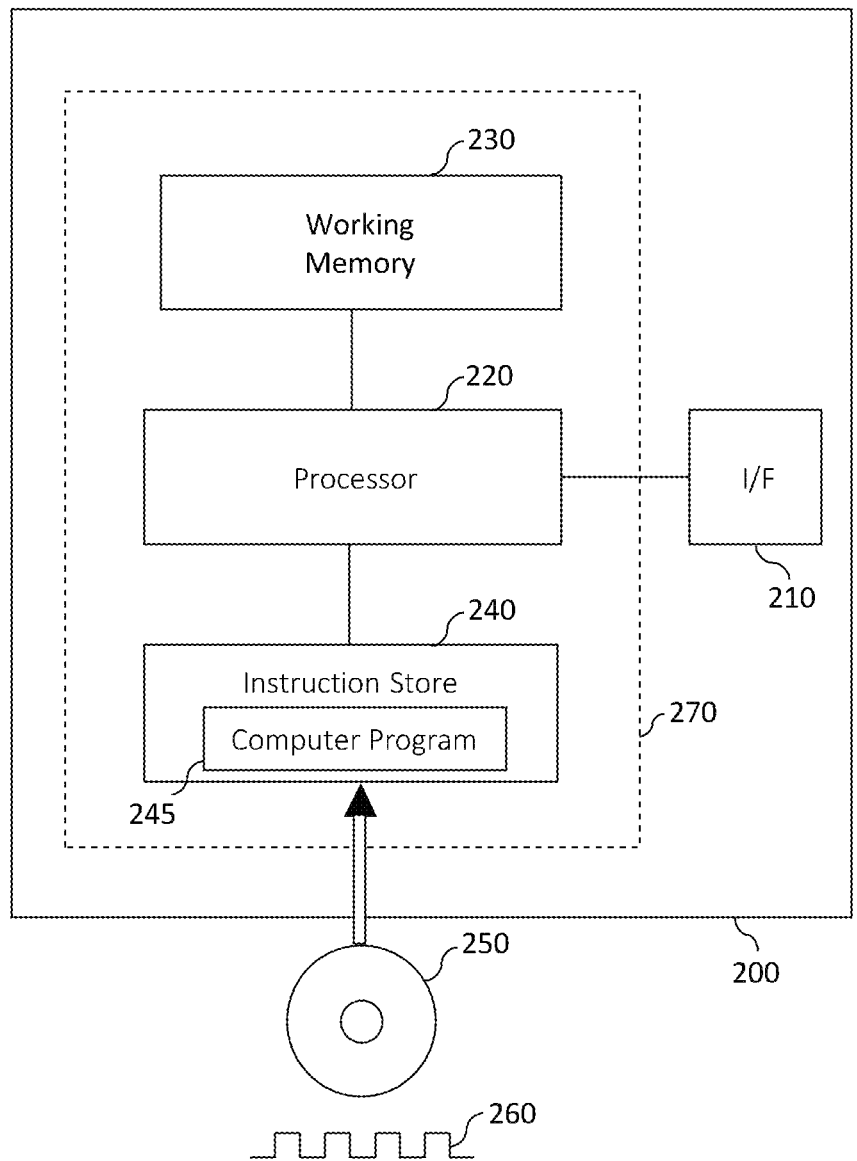
FIG. 4 illustrates an example implementation in programmable signal processing hardware of the first of the example embodiment herein.

FIG. 4 is a schematic illustration of a programmable signal processing hardware 200, which may be configured to perform the operations of the apparatus 100 of the first example embodiment.

The programmable signal processing apparatus 200 includes a communication interface (I/F) 210, for communicating with the fundus imaging apparatus and the OCT imaging system (or with the combined imaging system mentioned above, which is capable of generating both the image data $D_F$ defining the fundus image 10 and the OCT data $D_{OCT}$ of a subject retina) to receive the image data $D_F$ of the fundus image 10 and the OCT data $D_{OCT}$ therefrom. The signal processing apparatus 200 further includes a processor (e.g. a Central Processing Unit, CPU) 220, a working memory 230 (e.g. a random access memory) and an instruction store 240 storing a computer program 245 comprising computer-readable instructions which, when executed by the processor 220, cause the processor 220 to perform various functions of the apparatus 100 described herein. The working memory 230 stores information used by the processor 220 during execution of the computer program 245. The instruction store 240 may include a ROM (e.g. in the form of an electrically-erasable programmable read-only memory (EEPROM) or flash memory) which is pre-loaded with the computer-readable instructions. Alternatively, the instruction store 240 may include a RAM or similar type of memory, and the computer-readable instructions of the computer program 245 can be input thereto from a computer program product, such as a non-transitory, computer-readable storage medium 250 in the form of a CD-ROM, DVD-ROM, etc. or a computer-readable signal 260 carrying the computer-readable instructions. In any case, the computer program 245, when executed by the processor 220, causes the processor 220 to execute a method of processing the image data to include the supplementary information described herein. It should be noted, however, that the apparatus 100 may alternatively be implemented in non-programmable hardware, such as an application-specific integrated circuit (ASIC).

Figure 5:
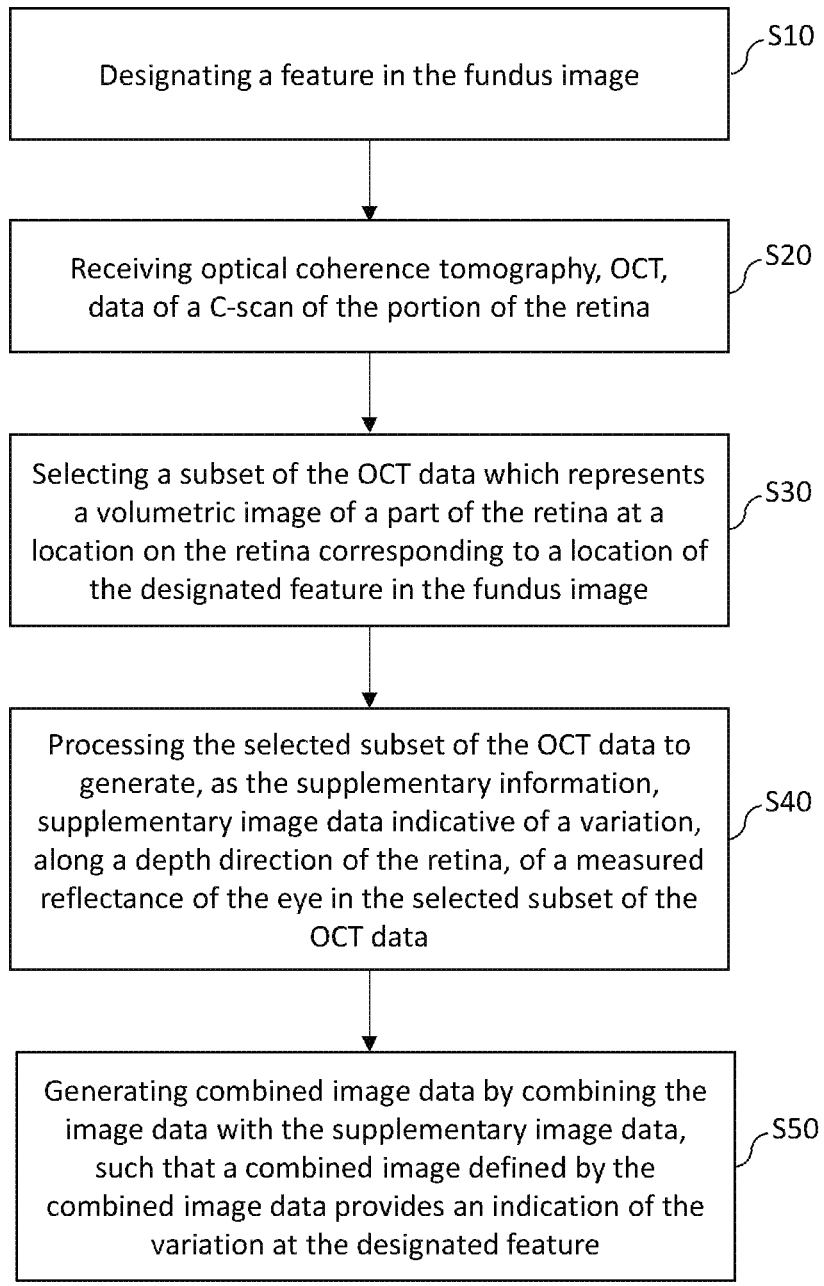
FIG. 5 is a flow diagram illustrating a process by which the apparatus of the first example embodiment processes image data defining a fundus image of a portion of a retina of an eye to include supplementary information on a designated feature in the fundus image.

FIG. 5 is a flow diagram illustrating a method by which the apparatus 100 of FIG. 1 processes the image data $D_F$ defining the fundus image 10 to include supplementary information on a designated feature 12 in the fundus image 10.

In process S10 of FIG. 5, the feature designation module 110 designates a feature 12 in the fundus image 10 of a portion of a retina that is defined by image data $D_F$ received from a fundus imaging apparatus, as described above.

In process S20 of FIG. 5, the receiver module 120 receives OCT data $D_{OCT}$ of an OCT C-scan of the portion of the retina, as described above. Although process S20 is illustrated to occur following process S10 in FIG. 5, it will be appreciated that the order in which these processes are performed may be reversed, and that at least parts of these processes may be performed concurrently.

In process S30 of FIG. 5, the section module 130 selects a subset $d_{OCT}$ of the received OCT data $D_{OCT}$ which represents a volumetric image of a part of the retina at a location on the retina corresponding to a location of the designated feature 12 in the fundus image 10, as described above.

In process S40 of FIG. 5, the supplementary image data generation module 140-1 processes the selected subset door of the OCT data $D_{OCT}$ to generate, as the supplementary information, supplementary image data $D_{SI}$ that is indicative of a variation, along a depth direction of the retina, of a measured reflectance of the eye in the selected subset $d_{OCT}$ of the OCT data $D_{OCT}$. In other words, the supplementary image data $D_{SI}$ indicates how the measured reflectance of the eye, as indicated by the voxels in the selected subset $d_{OCT}$ of the OCT data $D_{OCT}$, varies along the depth direction of the retina. The supplementary image data $D_{SI}$ may chart the variation of the measured reflectance of the eye, as indicated by the voxels in the selected subset $d_{OCT}$ of the OCT data $D_{OCT}$, with position along the depth direction of the retina. The supplementary image data $D_{SI}$ may thus provide a profile of the measured reflectance along the depth direction of the retina.

In the present example embodiment, the supplementary image data generation module 140-1 processes the selected subset $d_{OCT}$ of the OCT data $D_{OCT}$ to generate the supplementary image data $D_{SI}$ by a method which will now be described with reference to FIG. 6.

Figure 6:
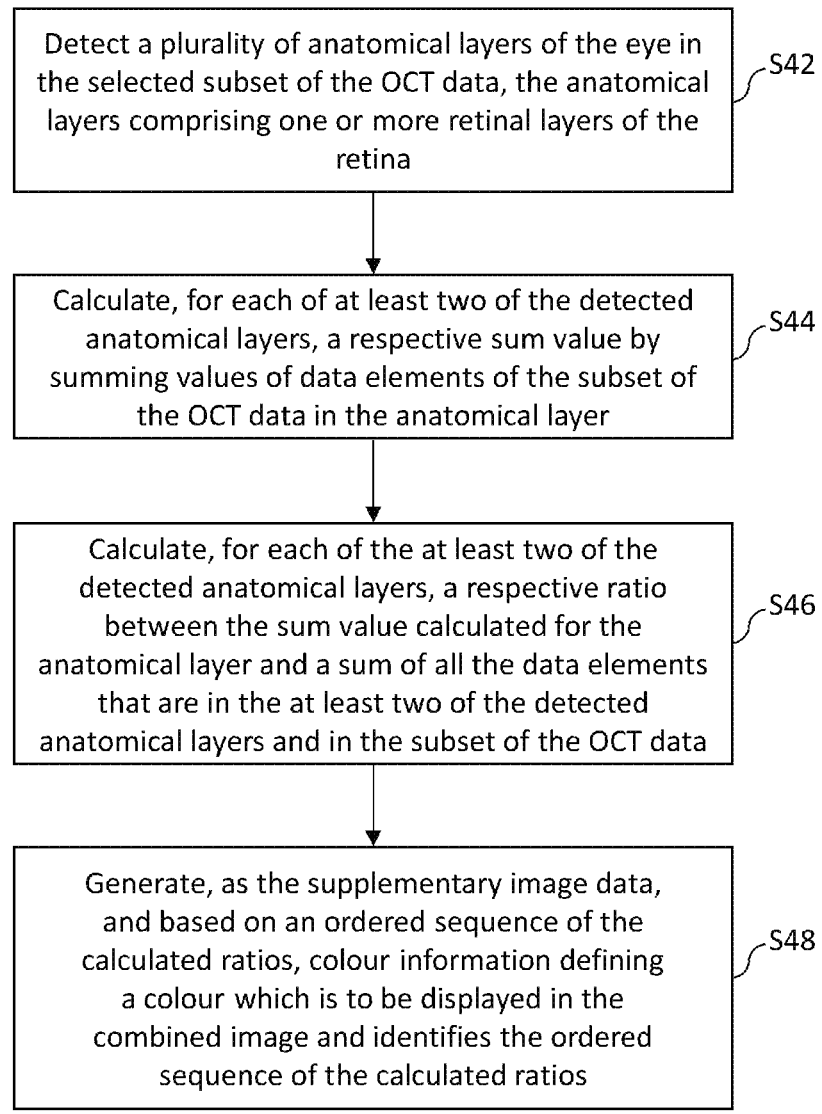
FIG. 6 is a flow diagram illustrating a process by which the supplementary image data generation module of the first example embodiment generates supplementary image data.

In process S42 of FIG. 6, the supplementary image data generation module 140-1 detects a plurality of anatomical layers in the selected subset $d_{OCT}$ of the OCT data $D_{OCT}$. The anatomical layers are anatomically distinct structures of the eye that overlie each other and may be distinguished in the depth axis of an OCT image because of differences in their light diffusive characteristics. The anatomical layers include anatomical layers that are present in the posterior segment of the eye, including one or more layers of the retina of the eye. Each layer has an inner surface and an outer surface (relative to the vitreous of the eye). The retina can be divided into 10 layers, namely: (1) the inner limiting membrane (ILM); (2) the nerve fiber layer (NFL); (3) the ganglion cell layer (GCL); (4) the inner plexiform layer (IPL); (5) the inner nuclear layer (INL); (6) the outer plexiform layer (OPL); (7) the outer nuclear layer (ONL); (8) the outer limiting membrane (OLM); (9) the photoreceptor layer (PL); and (10) the retinal pigmented epithelium (RPE) monolayer. The supplementary image data generation module 140-1 may detect the anatomical layers in the selected subset $d_{OCT}$ of the OCT data $D_{OCT}$ using one of a number of types of algorithm for ocular layer segmentation known to those skilled in the art, a review of which is provided in "A Review of Algorithms for Segmentation of Optical Coherence Tomography from Retina" by R. Kafieh et al, J Med Signals Sens. 2013 January-March; 3(1): 45-60. An anatomical layer segmentation algorithm is thus used in process S42 to generate layer identification information identifying the boundaries (i.e. an inner surface and an outer surface) of the detected anatomical layers in the selected subset $d_{OCT}$ of the OCT data $D_{OCT}$, which can be used to identify a respective set of data elements (voxels) in the selected subset $d_{OCT}$ of the OCT data $D_{OCT}$ belonging to each of the detected anatomical layers.

In process S44 of FIG. 6, the supplementary image data generation module 140-1 calculates, for each of the detected anatomical layers, a respective sum value by summing values of data elements (voxels) in the subset $d_{OCT}$ of the OCT data in the respective anatomical layer. In other words, the supplementary image data generation module 140-1 generates a sum value $S_i$ for each anatomical layer $L_i$ of the n detected anatomical layers, $L_1, \ldots L_n$, where n is an integer greater than or equal to 2, which have been identified using the anatomical layer identification information, by summing values of voxels that are located along the A-scans in the subset $d_{OCT}$ of the OCT data $D_{OCT}$ so as to be between the inner surface and the outer surface of the anatomical layer L.

In process S46 of FIG. 6, the supplementary image data generation module 140-1 calculates, for each anatomical layer $L_i$ of the detected anatomical layers $L_1, \ldots L_n$, a respective ratio $r_i$ between the sum value $S_i$ calculated for the anatomical layer $L_i$ and a sum, $S_{total}$, of all the data elements that are in the detected anatomical layers and in the subset $d_{OCT}$ of the OCT data $D_{OCT}$, i.e. $\Sigma_{i=1}^{n} S_i$.

In process S48 of FIG. 6, the supplementary image data generation module 140-1 generates colour information (as the supplementary image data $D_{SI}$) based on an ordered sequence of the calculated ratios $r_1$ to $r_n$, wherein the calculated ratios $r_1$ to $r_n$ are arranged in the same order as the order in which the corresponding anatomical layers are arranged in the posterior segment of the eye. The colour information is generated so as to define a colour to be displayed in the combined image that uniquely identifies the ordered sequence of the calculated ratios $r_1$ to $r_n$. The colour displayed in the combined image, at the location of the designated feature 12, is therefore indicative of the variation of the measured reflectance of the eye in the selected subset $d_{OCT}$ of the OCT data $D_{OCT}$ along the depth direction of the retina.

It should be noted that processes S44 to S48 in FIG. 6 need not operate on all of the anatomical layers in the selected subset $d_{OCT}$ of the OCT data $D_{OCT}$ that have been detected in process S42 of FIG. 6, and may instead operate on at least two of these anatomical layers. Processes S44 to S48 in FIG. 6 operate on one or more detected anatomical layers forming part of the retina, and may additionally operate on one or more anatomical layers that do not form part of the retina, such as a sub-retinal layer which includes the choroid and pathological sub-retinal fluid, for example.

By way of example, in the present example embodiment, a first anatomical layer $L_1$, a second anatomical layer $L_2$, and a third anatomical layer $L_3$ are detected by the supplementary image data generation module 140-1 in process S42 of FIG. 6. In process S44 of FIG. 6, the supplementary image data generation module 140-1 generates respective sum values $S_1$, $S_2$ and $S_3$ for the anatomical layers $L_1$, $L_2$ and $L_3$, and calculates (in process S46 of FIG. 6) respective ratios $r_1$, $r_2$ and $r_3$ for the anatomical layers $L_1$, $L_2$ and $L_3$. For example, $r_1$ is calculated as $S_1/(S_1+S_2+S_3)$. In process S48 in FIG. 6 of this example, the supplementary image data generation module 140-1 generates the colour information by assigning, to each of a red colour component R, a green colour component G and a blue colour component B of the colour to be displayed in the combined image, a respective weighting, $w_R$, $w_G$ or $w_B$, for the colour component in accordance with a respective one of the calculated ratios $r_1$, $r_2$ or $r_3$ in the ordered sequence $r_1$; $r_2$; $r_3$ of the calculated ratios. For instance, in an example where the ratios calculated in process S46 of FIG. 6 are $r_1$=0.1, $r_2$=0.85 and $r_3$=0.05, indicating that anatomical layer $L_2$ provides a dominant contribution to the measured reflectance represented by the data element values in the subset $d_{OCT}$ of the OCT data $D_{OCT}$, the assignment of corresponding weightings 0.1:0.85:0.05 to the RGB colour components results in the colour that is to be displayed in the combined image being predominantly green, which indicates to a viewer of the combined image that anatomical layer $L_2$ provides a dominant contribution to the measured reflectance of the designated feature 12. In another example, the display of a yellow colour in the combined image would indicate that anatomical layers $L_1$ and $L_2$ provide the main contribution to the measured reflectance. In a further example, the display of a cyan colour in the combined image would indicate that layers $L_2$ and $L_3$ provide the main contribution to the measured reflectance.

Referring again to FIG. 5, in process S50, the combined image data generation module 150 generates the combined image data $D_{CI}$ by combining the image data $D_F$ with the supplementary image data $D_{SI}$, such that a combined image defined by the combined image data $D_{CI}$ provides an indication of the variation at the designated feature 12. The combined image data generation module 150 may be arranged to generate the combined image data $D_{CI}$ by replacing pixel values of a subset of pixels of the fundus image data $D_F$ with pixel values of the supplementary image data $D_{SI}$, such that a combined image defined by the combined image data $D_{CI}$ provides an indication of the variation of the measured reflectance of the eye in the selected subset $d_{OCT}$ of the OCT data $D_{OCT}$ at the designated feature 12. In example embodiments like the present example embodiment, the combined image data generation module 150 may be arranged to generate the combined image data $D_{CI}$ by replacing pixel values of a subset of pixels of the fundus image data $D_F$, which subset of pixels defines a subregion of the fundus image which is at the location of the designated feature 12 in the fundus image 10, with pixel values of the supplementary image data $D_{SI}$, such that a combined image defined by the combined image data $D_{CI}$ provides an indication of the variation of the measured reflectance of the eye in the selected subset $d_{OCT}$ of the OCT data $D_{OCT}$ at the designated feature 12. More specifically, the combined image data generation module 150 may, as in the present example embodiment, generate the combined image data $D_{CI}$ by modifying the image data $D_F$ such that pixel values in the fundus image 10, which are at pixel locations corresponding to pixel locations in the OCT en-face image 30 showing data from the selected subset $d_{OCT}$ of the OCT data $D_{OCT}$, are replaced by pixel values representing the colour determined by the supplementary image data generation module 140-1 for that subset $d_{OCT}$ of the OCT data $D_{OCT}$. The aforementioned correspondence between pixel locations in the fundus image 10 and the OCT en-face image 30 may be determined by the geometric transformation discussed above.

Figure 7:
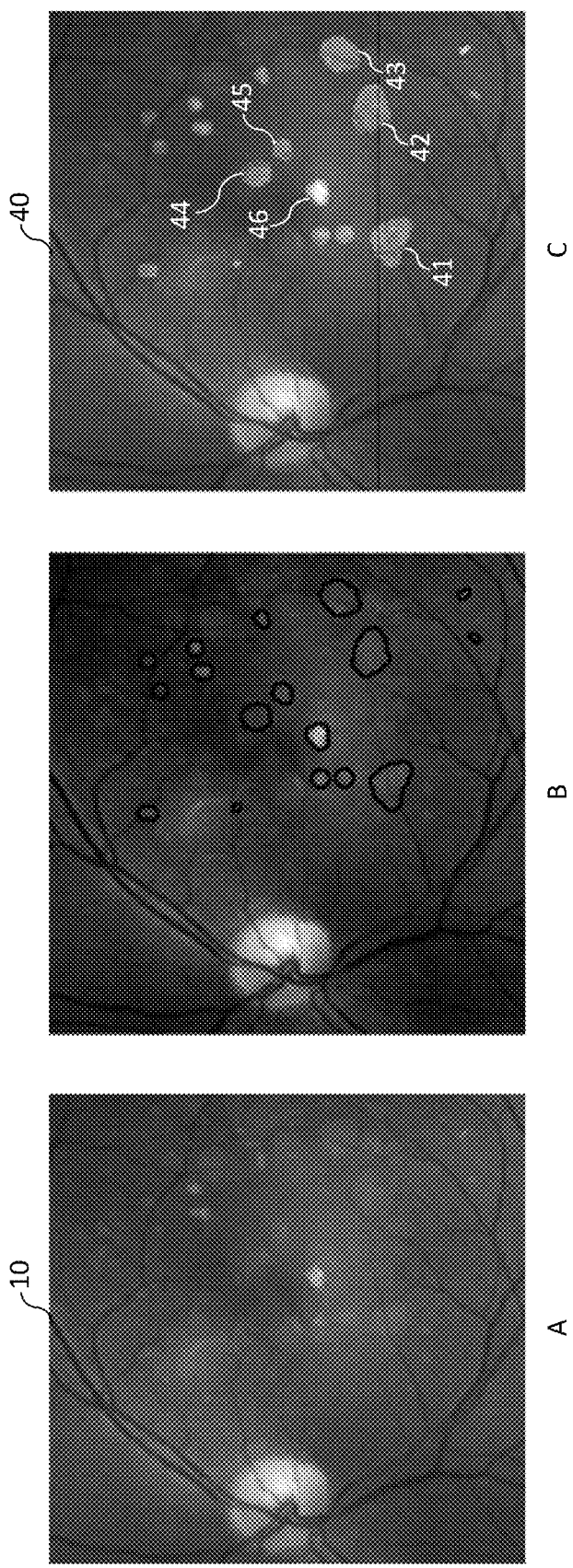
FIG. 7 shows a fundus image (image A), a processed version of the fundus image in which designated features are highlighted (image B), and a combined image (image C) generated by the apparatus of the first example embodiment.

Image A in FIG. 7 is an example of a fundus image 10, which shows several features of interest that are highlighted in image B of FIG. 7. The curves bounding the features of interest that are shown in image B are based on an output from a feature extraction algorithm. Image C of FIG. 7 is an example of a combined image 40, wherein the regions of the fundus image 10 highlighted in image B are coloured in accordance with the colour information generated by the supplementary image data generation module 140-1. In image C, regions 41, 42 and 43 are predominantly blue, regions 44 and 45 are predominantly red, region 46 is predominantly white, and the remaining regions are predominantly green.

Figure 8:
FIG. 8 shows an image of a B-scan taken along the horizontal line shown in image C of FIG. 7.

This colouring indicates that regions 41-43 relate to features of the retina that are nearest the (inner) retinal surface, specifically within the inner and outer neurological retina, which is a first anatomical layer detected in this example. FIG. 8 shows an image of a B-scan taken along the horizontal line in image C of FIG. 7. Regions of the retina in FIG. 8, which correspond to those in FIG. 7 where the horizontal line crosses regions 41 and 42, have a higher reflectance near the inner surface of the retina (towards the top of FIG. 8) than the surrounding regions of the retina in FIG. 8.

In FIG. 7, the predominantly green regions relate to features of a deeper retinal layer that is detected in this example, which is the retinal pigment epithelium (RPE) in this example. Regions 44 and 45 relate to yet deeper features that are farthest the retinal surface, and lie within the choroid or pathological subretinal fluid, which are in the third anatomical layer that is detected in this example.

Second Example Embodiment

Figure 9:
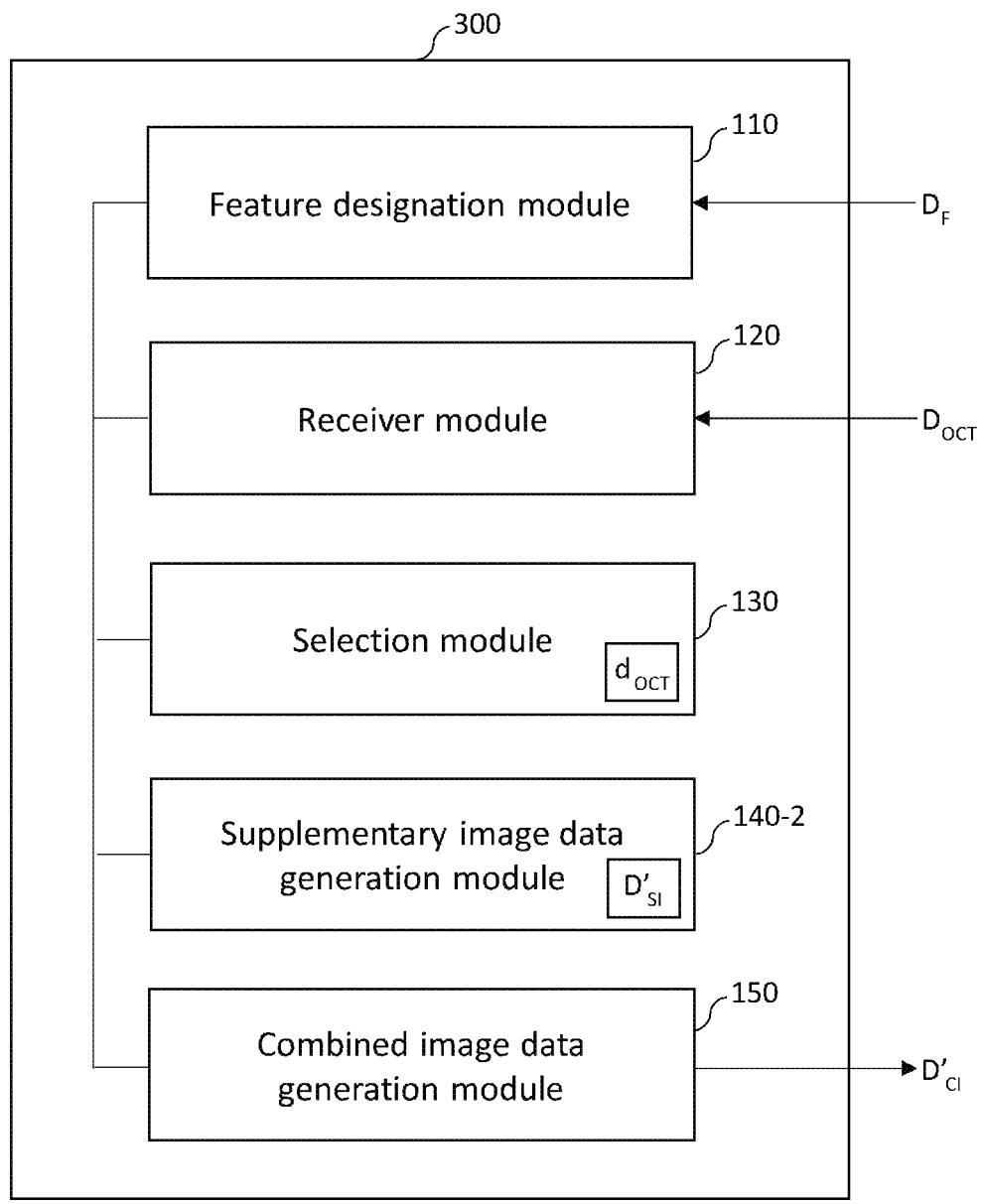
FIG. 9 is a schematic illustration of an apparatus for processing image data, according to a second example embodiment.

FIG. 9 is a schematic illustration of an apparatus 300 for processing image data according to a second example embodiment. The apparatus 300 of the second example embodiment differs from the apparatus 100 of the first example embodiment by the arrangement of the supplementary image data generation module 140-2, which is arranged to generate a different kind of supplementary image data, $D'_{SI}$. In all other respects, the apparatus 300 of the second example embodiment is the same as apparatus 100 of the first example embodiment, as described above.

In the present example embodiment, the supplementary image data generation module 140-2 processes the selected subset $d_{OCT}$ of the OCT data $D_{OCT}$ to generate the supplementary image data $D'_{SI}$ by a method which is a variant of the method described above with reference to FIG. 6, and which will now be described with reference to FIG. 10.

Figure 10:
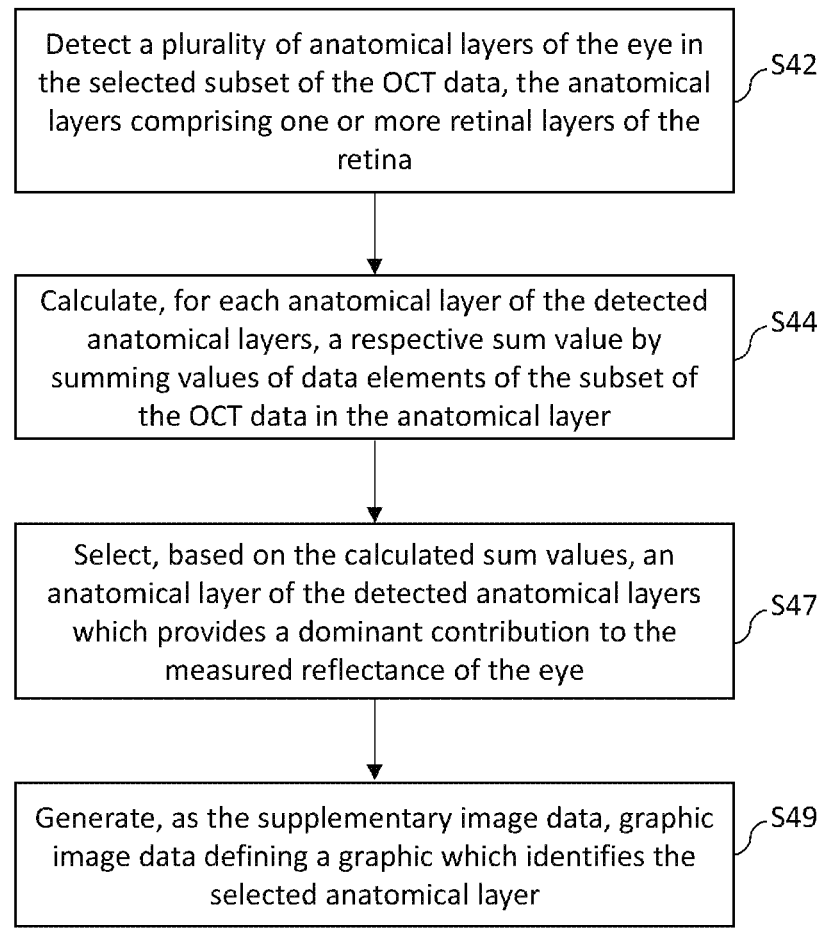
FIG. 10 is a flow diagram illustrating a process by which the supplementary image data generation module of the second example embodiment generates supplementary image data.

Processes S42 and S44 in FIG. 10 are the same as processes S42 and S44 in FIG. 6, and will therefore not be described again here.

In process S47 of FIG. 10, the supplementary image data generation module 140-2 selects, based on the sum values calculated in process S44, an anatomical (e.g. retinal) layer of the detected layers $L_1$ to $L_n$ which provides a dominant contribution to the measured reflectance of the among the detected layers for which the sum values have been calculated. The supplementary image data generation module 140-2 may, as in the present example embodiment, select the anatomical layer that provides a dominant contribution by selecting the layer for which the calculated sum value is largest among the detected layers for which the sum values have been calculated.

In process S49 of FIG. 10, the supplementary image data generation module 140-2 generates, as the supplementary image data $D'_{SI}$, graphic image data defining a graphic which identifies the selected anatomical layer, for example by a text label naming the layer (in full or in an abbreviated form, for example). The graphic need not such a self-contained identification of the selected anatomical layer, however, and may comprise a pattern, for example, which the viewer can use to identify the selected anatomical layer by reference to a legend (showing an association between different forms (e.g. patterns) of the graphic and corresponding named anatomical layers) that is also displayed on the screen.

The combined image data generation module 150 is arranged to generate the combined image data $D'_{CI}$ by combining the image data $D_F$ with the graphic image data such that the combined image is an annotated version of the fundus image 10, wherein the graphic is overlaid on the fundus image 10 (and preferably shaped, for example to have a pointed feature such as an arrow or the like) so as to indicate the location of designated feature 12. Examples of such an annotated version of the fundus image 10 are shown in FIGS. 11 and 12.

Thus, in some example embodiments like the present example embodiment, the combined image data generation module 150 may be arranged to generate the combined image data $D'_{CI}$ by replacing pixel values of a subset of pixels of the fundus image data with pixel values of the supplementary image data $D'_{SI}$, such that a combined image defined by the combined image data $D'_{CI}$ provides an indication of the variation of the measured reflectance of the eye in the selected subset of the OCT data at the designated feature 12. The supplementary image data generation module 140-2 may be arranged to generate supplementary image data which defines a graphic that is indicative of the variation, along the depth direction of the retina, of the measured reflectance of the eye in the selected subset of the OCT data or, more particularly, how the measured reflectance of the eye, as indicated in the selected subset of the OCT data varies along a depth direction of the retina. In example embodiments like the present example embodiment, the combined image data generation module 150 may be arranged to generate the combined image data $D'_{CI}$ by replacing pixel values of a subset of pixels of the fundus image data with pixel values of the supplementary image data $D'_{SI}$ such that a combined image defined by the combined image data $D'_{CI}$ comprises the graphic, which is overlaid on the fundus image 10 so as to provide an indication of the variation of the measured reflectance of the eye in the selected subset of the OCT data at the designated feature 12.

Figure 11:
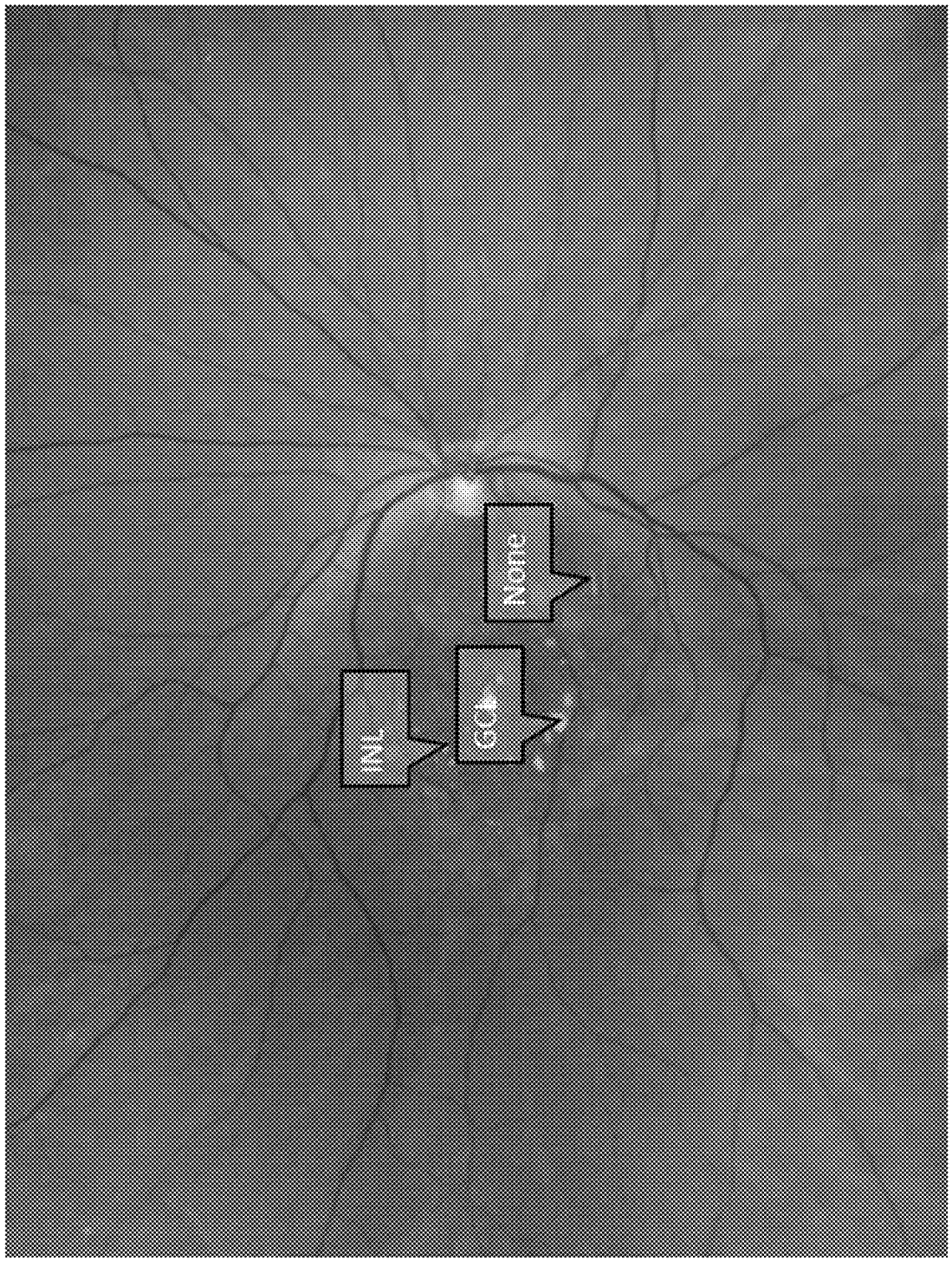
FIG. 11 shows a first example of a combined image generated by the apparatus of the second example embodiment.

In FIG. 11, the label "INL" is overlaid on the fundus image so as to indicate the location in the fundus image of a feature that is located in the inner nuclear layer (INL) of the retina, while the label "GCL" is overlaid on the fundus image so as to indicate the location in the fundus image of a feature that is located in the ganglion cell layer (GCL) of the retina. The label "None" is overlaid on the fundus image indicates that the associated feature in the fundus image is not located within any layer of the retina.

Figure 12:
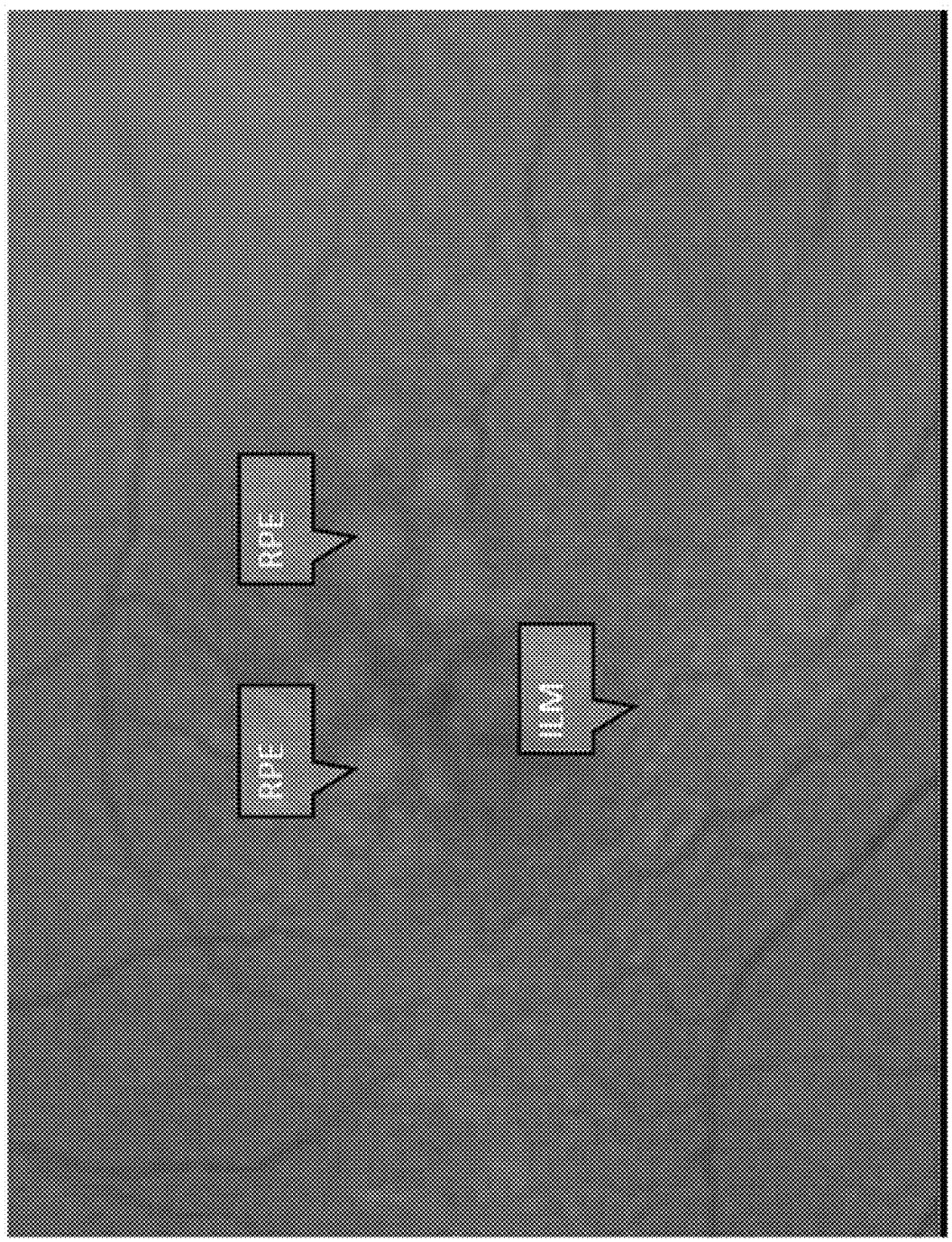
FIG. 12 shows a second example of a combined image generated by the apparatus of the second example embodiment.

In FIG. 12, the label "RPE" is overlaid on the fundus image so as to indicate the location in the fundus image of a feature that is located in the retinal pigment epithelium (RPE) of the retina, while the label "ILM" is overlaid on the fundus image so as to indicate the location in the fundus image of a feature that is located in the inner limiting membrane (ILM) that lies between the retina and the vitreous body.

Third Example Embodiment

Figure 13:
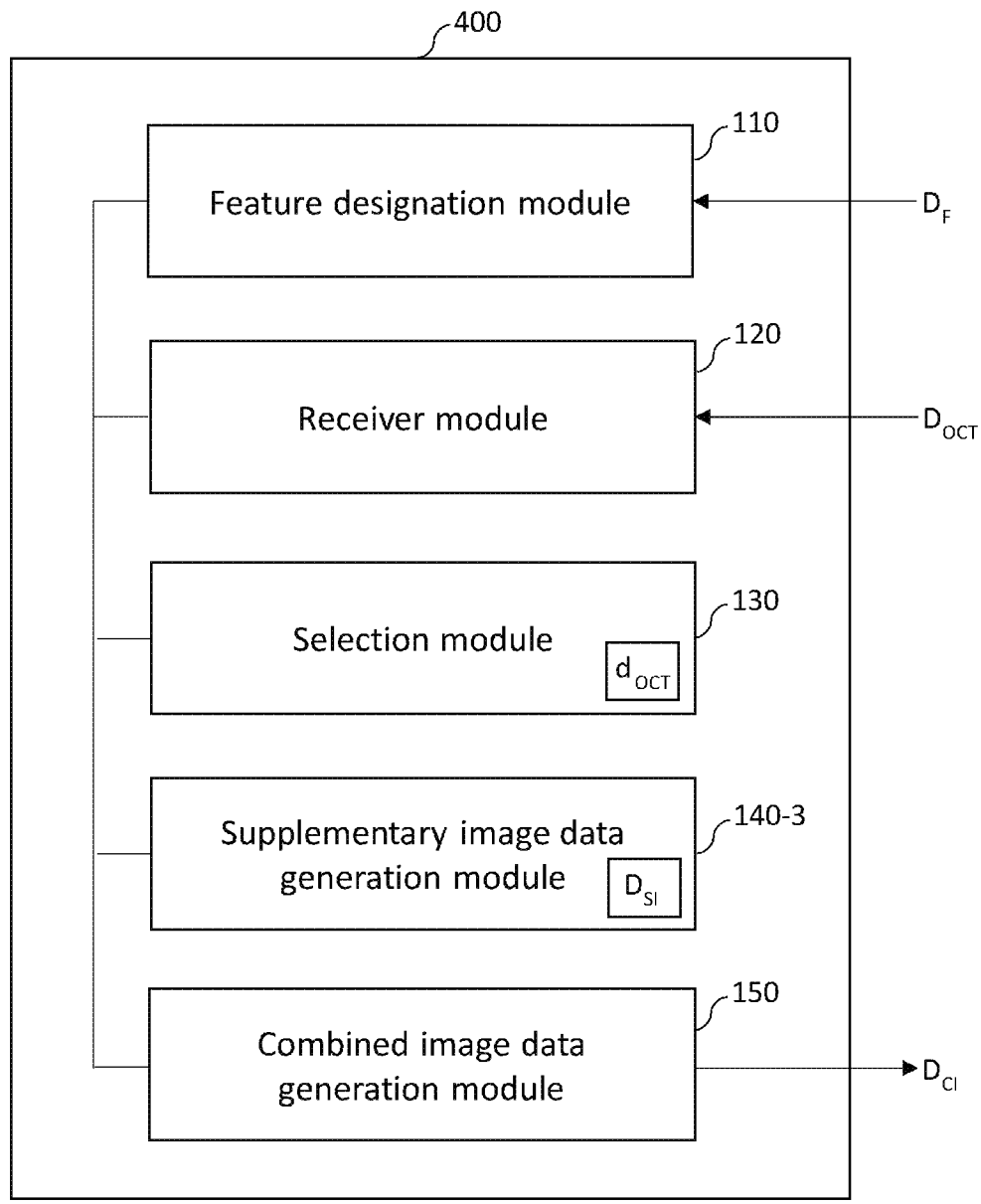
FIG. 13 is a schematic illustration of an apparatus for processing image data, according to a third example embodiment.

FIG. 13 is a schematic illustration of an apparatus 400 for processing image data according to a third example embodiment. The apparatus 400 of the third example embodiment differs from the apparatus of the first and second example embodiments by the arrangement of the supplementary image data generation module 140-3, which is arranged to generate the supplementary information described in these example embodiments in a different way. In all other respects, the apparatus 400 of the third example embodiment is the same as apparatus 100 of the first example embodiment and apparatus 300 of the second example embodiment, as described above.

In the present example embodiment, the selected subset $d_{OCT}$ of the OCT data $D_{OCT}$ represents a volumetric image of a part of the retina (possibly in addition to another part of the for example beneath the outer surface of the retina) having a feature of a predetermined type and is processed by the supplementary image data generation module 140-3 to generate the supplementary image data $D_{SI}$ by a method which will now be described with reference to FIG. 14.

Figure 14:
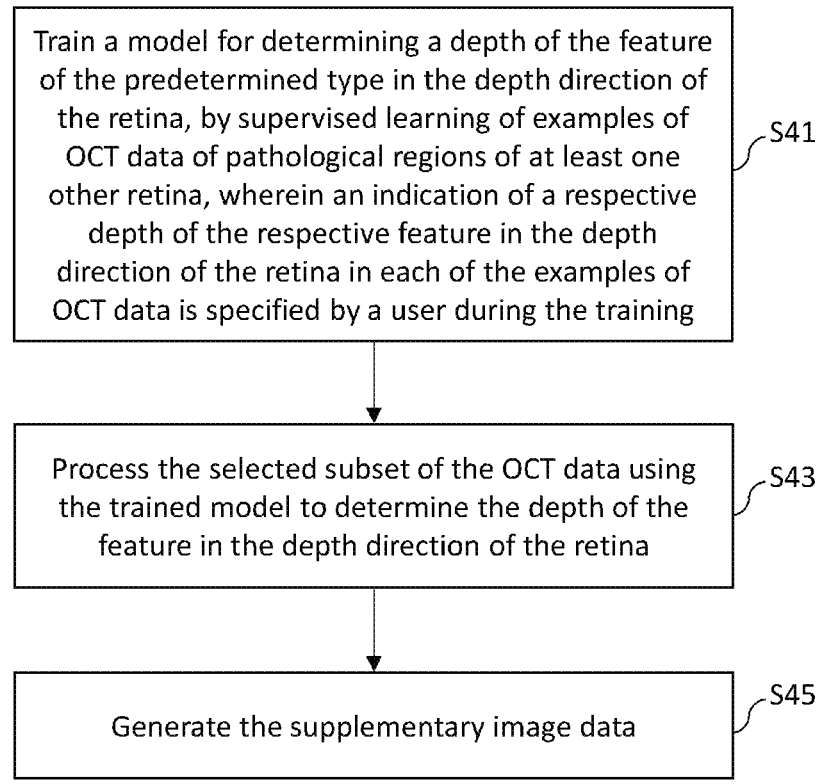
FIG. 14 is a flow diagram illustrating a process by which the supplementary image data generation module of the third example embodiment generates supplementary image data.

In process S41 of FIG. 14, a model for determining a depth of the feature of the predetermined type in the depth direction of the retina is trained by supervised learning of examples of OCT data of pathological regions of at least one other retina. Each of these examples of OCT data comprises a single OCT A-scan or two or more adjacent OCT A-scans, and each of the pathological regions has a respective feature of the predetermined type. While the model is being trained, an indication of a respective depth of the respective feature in the depth direction of the retina in each of the examples of OCT data is specified by a user. The model may also be provided with the locations of retinal layers in the A-scan(s) and, in the training process, the model may learn to output the depth of the feature when given the A-scan (or a group of adjacent A-scans) and the layers as input.

The depth of the feature may be specified in several ways. The depth is usually defined relative to one or more retinal layers. For example, the depth may be defined in terms of a number of pixels or as a linear measurement (assuming pixel dimensions have been previously estimated) relative to one of the retinal layers. The innermost or outermost retinal surfaces may provide suitable reference points for this measurement. Alternatively, the depth may be defined relative to multiple retinal layers which have been identified by automated means. In this case, the depth may be indicated by the name of the layer that the feature is in and, optionally, the displacement of the feature relative to the inner or outer surface of the layer. Also, the depth may be indicated by the name of the layer that the feature is in and a unitless normalised displacement of the feature relative to both inner and outer surfaces of the layer, e.g. such that 0 indicates being at the inner surface of the layer and 1 indicates being at the outer surface of the layer.

In process S43 of FIG. 14, the supplementary image data generation module 140-3 processes the selected subset $d_{OCT}$ of the OCT data $D_{OCT}$ by using the model that has been trained in process S41 to determine the depth of the feature in the depth direction of the retina.

In process S45 of FIG. 14, the supplementary image data generation module 140-3 generates, as the supplementary image data, either (i) graphic image data defining a graphic which indicates the determined depth of the feature and is to be overlaid on the fundus image 10 so as to indicate a location of the feature in the combined image 40, or (ii) colour information defining a colour which is to be displayed at a location of the feature in the combined image and indicates the determined depth of the feature. The graphic image data and the colour information may be generated as described above.

There has been described, in accordance with example embodiments herein, an apparatus as set out in E1 to E12 below.

E1. An apparatus 100 for processing image data defining a fundus image 10 of a portion of a retina of an eye to include supplementary information on a designated feature 12 in the fundus image 10, the apparatus comprising:
a feature designation module 110 arranged to designate a feature in the fundus image 10;
a receiver module 120 arranged to receive optical coherence tomography, OCT, data $D_{OCT}$ of a C-scan 20 of the portion of the retina;
a selection module 130 arranged to select a subset $d_{OCT}$ of the OCT data $D_{OCT}$ which represents a volumetric image of a part of the retina at a location on the retina corresponding to a location of the designated feature 12 in the fundus image 10;
a supplementary image data generation module 140-1 arranged to process the selected subset $d_{OCT}$ of the OCT data $D_{OCT}$ to generate, as the supplementary information, supplementary image data $D_{SI}$ indicative of a variation, along a depth direction of the retina, of a measured reflectance of the eye in the selected subset $d_{OCT}$ of the OCT data $D_{OCT}$; and
a combined image data generation module 150 arranged to generate combined image data $D_{CI}$ by combining the image data $D_F$ with the supplementary image data $D_{SI}$, such that a combined image defined by the combined image data $D_{CI}$ provides an indication of the variation at the designated feature 12.

E2. The apparatus according to E1, wherein the feature designation module 110 is arranged to cause the fundus image 10 and a cursor 16 to be displayed on a display 14, such that the cursor 16 can be controlled to move over the displayed fundus image 10 by a signal from a user input device 18, and to designate the feature 12 in the fundus image 10 by recording, in response to a feature designation command, a value of a first location indicator that is indicative of a display location of the cursor 16 on the displayed fundus image 10.

E3. The apparatus according to E2, wherein the selection module 130 is arranged to process the OCT data $D_{OCT}$ to generate an OCT en-face image 30 of the portion of the retina, cause the OCT en-face image 30 to be displayed on the display 14 together with the fundus image 10, such that the cursor 16 can be controlled to move over the displayed OCT en-face image 30 by the signal from the user input device 18, and select the subset $d_{OCT}$ of the OCT data $D_{OCT}$ based on a value of a second location indicator, which is indicative of a display location of the cursor 16 when the cursor 16 has been guided by the signal from the user input device 18 to overlay a part of the displayed OCT en-face image 30 which corresponds to the designated feature 12 in the displayed fundus image 10.

E4. The apparatus according to E1, wherein the feature designation module 110 is arranged to designate the feature 12 in the fundus image 10 automatically using a feature extraction algorithm.

E5. The apparatus according to E4, wherein the selection module 130 is arranged to:
cause the fundus image 10 and a feature location indicator 19, which indicates a location of the designated feature 12 in the fundus image 10, to be displayed on a display 14;
process the OCT data $D_{OCT}$ to generate an OCT en-face image 30 of the portion of the retina;
cause the OCT en-face image 30 and a cursor 16 to be displayed on the display 14 together with the fundus image 10, such that the cursor 16 can be controlled to move over the displayed OCT en-face image 30 by a signal from a user input device 18; and
select the subset $d_{OCT}$ of the OCT data $D_{OCT}$ based on a value of a second location indicator, which is indicative of a display location of the cursor 16 when the cursor 16 has been guided by the signal from the user input device 18 to overlay a part of the displayed OCT en-face image 30 whose location corresponds to the location of the designated feature 12 in the fundus image 10 that is indicated by the feature location indicator 19.

E6. The apparatus according to E4, wherein the selection module 130 is arranged to select the subset $d_{OCT}$ of the OCT data $D_{OCT}$ by applying a geometric transformation, which maps locations in the fundus image 10 to corresponding A-scan locations in the OCT data $D_{OCT}$, to the location of the feature 12 in the fundus image 10 which has been designated by the feature extraction algorithm.

E7. The apparatus according to any of E1 to E6, wherein the feature 12 is one of a dot and a hyper-reflective dot in the fundus image 10, the feature 12 having a pathological cause or being caused by a reflection from an inner limiting membrane of the retina.

E8. The apparatus according to E7, wherein the feature 12 has a pathological cause comprising one of blood leakage, exudation, drusen, atrophy and/or naevi in the retina, and atrophy of a retinal pigment epithelium in the retina.

E9. The apparatus according to any of E1 to E8, wherein the supplementary image data generation module 140-1 is arranged to process the selected subset $d_{OCT}$ of the OCT data $D_{OCT}$ to generate the supplementary image data $D_{SI}$ by:
detecting S42 a plurality of anatomical layers of the eye in the selected subset $d_{OCT}$ of the OCT data $D_{OCT}$;
calculating S44, for each of at least two of the detected anatomical layers, a respective sum value by summing values of data elements of the subset $d_{OCT}$ of the OCT data $D_{OCT}$ in the anatomical layer;
calculating S46, for each of the at least two of the detected anatomical layers, a respective ratio between the sum value calculated for the anatomical layer and a sum of all the data elements that are in the at least two of the detected anatomical layers and in the subset $d_{OCT}$ of the OCT data $D_{OCT}$; and
generating S48, as the supplementary image data $D_{SI}$, and based on an ordered sequence of the calculated ratios, wherein the calculated ratios are arranged in order of the corresponding anatomical layers in the eye, colour information defining a colour which is to be displayed in the combined image and identifies the ordered sequence of the calculated ratios, such that the colour is indicative of the variation, along the depth direction of the retina, of the measured reflectance of the eye in the selected subset $d_{OCT}$ of the OCT data $D_{OCT}$.

E10. The apparatus according to E9, wherein the supplementary image data generation module 140-1 is arranged to:
detect three anatomical layers in the selected subset $d_{OCT}$ of the OCT data $D_{OCT}$; and generate the colour information by assigning, to each of a red colour component, a green colour component and a blue colour component of the colour to be displayed in the combined image, a respective weighting for the colour component in accordance with a respective one of the calculated ratios in the ordered sequence of the calculated ratios.

E11. The apparatus according to any of E1 to E8, wherein the supplementary image data generation module 140-2 is arranged to process the selected subset $d_{OCT}$ of the OCT data $D_{OCT}$ to generate the supplementary image data $D_{SI}$ by:
- detecting a plurality of anatomical layers of the eye in the selected subset $d_{OCT}$ of the OCT data $D_{OCT}$;
- calculating, for each anatomical layer of the detected anatomical layers, a respective sum value by summing values of data elements of the subset $d_{OCT}$ of the OCT data $D_{OCT}$ in the anatomical layer;
- selecting, based on the calculated sum values, an anatomical layer of the detected anatomical layers which provides a dominant contribution to the measured reflectance of the eye; and
- generating, as the supplementary image data $D_{SI}$, graphic image data defining a graphic which identifies the selected anatomical layer, and
- wherein the combined image data $D_{CI}$ is generated by combining the image data $D_F$ with the graphic image data such that, in the combined image, the graphic is overlaid on the fundus image 10 at the designated feature 12.

E12. The apparatus according to any of E1 to E8, wherein the selected subset $d_{OCT}$ of the OCT data $D_{OCT}$ represents a volumetric image of a part of the retina having a feature of a predetermined type, and the supplementary image data generation module 140-3 is arranged to generate the supplementary image data $D_{SI}$ by:
- training a model for determining a depth of the feature of the predetermined type in the retina, by supervised learning of examples of OCT data of pathological regions of at least one other retina, each of the examples of OCT data comprising a single OCT A-scan or two or more adjacent OCT A-scans, and each of the pathological regions having a respective feature of the predetermined type, wherein an indication of a respective depth of the respective feature in the retina in each of the examples of OCT data is specified by a user during the training;
- processing the selected subset door of the OCT data $D_{OCT}$ using the trained model to determine the depth of the feature in the retina; and
- generating, as the supplementary image data, one of
  - graphic image data defining a graphic which indicates the determined depth of the feature in the retina and is to be overlaid on the fundus image 10 so as to indicate a location of the feature in the combined image 40, and
  - colour information defining a colour which is to be displayed at a location of the feature in the combined image and indicates the determined depth of the feature in the retina.

The example aspects described here avoid limitations, specifically rooted in computer technology, relating to the processing of retinal fundus images. In particular, features of some common eye diseases have similar appearance in fundus images, which may be difficult to disambiguate from specular imaging artefacts and the like. By virtue of the example aspects described herein, additional information in OCT data may be leveraged for a clearer rendering of features in fundus images, which can be assimilated by a user without needing to review OCT data, and which can help the user to avoid misinterpretation of artefactual spots and the like in fundus images. Also, by virtue of the foregoing capabilities of the example aspects described herein, which are rooted in computer technology, the example aspects described herein improve computers and computer processing/functionality, and also improve the field(s) of at least retinal image analysis.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized (and navigated) in ways other than those shown in the accompanying figures.

Software embodiments of the examples presented herein may be provided as a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g. program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects herein, as described above.

Included in the programming and/or software of the system are software modules for implementing the procedures described herein. In some example embodiments herein, a module includes software, although in other example embodiments herein, a module includes hardware, or a combination of hardware and software.

While various example embodiments have been described above, it should be understood that they have been presented by way of example, and not limitation. It will be apparent to persons skilled in the relevant art(s) that various changes in form and detail can be made therein. Thus, the present disclosure should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that the procedures recited in the claims need not be performed in the order presented.

While this specification contains many specific embodiment details, these should not be construed as limiting, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

Having now described some illustrative embodiments and embodiments, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one embodiment are not intended to be excluded from a similar role in other embodiments or embodiments.

The apparatus and computer programs described herein may be embodied in other specific forms without departing from the characteristics thereof. The foregoing embodiments are illustrative rather than limiting of the described systems and methods. Scope of the apparatus and computer programs described herein is thus indicated by the appended claims, rather than the foregoing description, and changes that come within the meaning and range of equivalency of the claims are embraced therein.

The invention claimed is:

1. A computer-implemented method of processing image data defining a fundus image of a portion of a retina of an eye to include supplementary information on a designated feature in the fundus image, the method comprising:
   designating a feature in the fundus image;
   receiving optical coherence tomography, OCT, data of a C-scan of the portion of the retina;
   selecting a subset of the OCT data which represents a volumetric image of a part of the retina at a location on the retina corresponding to a location of the designated feature in the fundus image;
   processing the selected subset of the OCT data to generate, as the supplementary information, supplementary image data indicative of a variation, along a depth direction of the retina, of a measured reflectance of the eye in the selected subset of the OCT data; and
   generating combined image data by combining the image data with the supplementary image data, such that a combined image defined by the combined image data provides an indication of the variation at the designated feature.

2. The computer-implemented method according to claim 1, further comprising:
   causing the fundus image and a cursor to be displayed on a display, such that the cursor can be controlled to move over the displayed fundus image by a signal from a user input device,
   wherein the feature in the fundus image is designated by recording, in response to a feature designation command, a value of a first location indicator that is indicative of a display location of the cursor on the displayed fundus image.

3. The computer-implemented method according to claim 2, further comprising:
   processing the OCT data to generate an OCT en-face image of the portion of the retina; and
   causing the OCT en-face image to be displayed on the display together with the fundus image, such that the cursor can be controlled to move over the displayed OCT en-face image by the signal from the user input device,
   wherein the subset of the OCT data is selected based on a value of a second location indicator, which is indicative of a display location of the cursor when the cursor has been guided by the signal from the user input device to overlay a part of the displayed OCT en-face image which corresponds to the designated feature in the displayed fundus image.

4. The computer-implemented method according to claim 1, wherein the feature in the fundus image is designated automatically by a feature extraction algorithm.

5. The computer-implemented method according to claim 4, further comprising:
causing the fundus image and a feature location indicator, which indicates the location of the designated feature in the fundus image, to be displayed on a display;
processing the OCT data to generate an OCT en-face image of the portion of the retina; and
causing the OCT en-face image and a cursor to be displayed on the display together with the fundus image, such that the cursor can be controlled to move over the displayed OCT en-face image by a signal from a user input device,
wherein the subset of the OCT data is selected based on a value of a second location indicator, which is indicative of a display location of the cursor when the cursor has been guided by the signal from the user input device to overlay a part of the displayed OCT en-face image whose location corresponds to the location of the designated feature in the fundus image that is indicated by the feature location indicator.

6. The computer-implemented method according to claim 4, wherein the subset of the OCT data is selected by applying a geometric transformation, which maps locations in the fundus image to corresponding A-scan locations in the OCT data, to the location of the feature in the fundus image which has been designated by the feature extraction algorithm.

7. The computer-implemented method according to claim 1, wherein the feature is one of a dot and a hyper-reflective dot in the fundus image, the feature having a pathological cause or being caused by a reflection from an inner limiting membrane of the retina.

8. The computer-implemented method according to claim 7, wherein the feature has a pathological cause comprising one of blood leakage, exudation, drusen, atrophy and/or naevi in the retina, and atrophy of a retinal pigment epithelium in the retina.

9. The computer-implemented method according to claim 1, wherein the selected subset of the OCT data is processed to generate the supplementary image data by:
detecting a plurality of anatomical layers of the eye in the selected subset of the OCT data, the anatomical layers comprising one or more retinal layers of the retina;
calculating, for each of at least two of the detected anatomical layers, a respective sum value by summing values of data elements of the subset of the OCT data in the anatomical layer;
calculating, for each of the at least two of the detected anatomical layers, a respective ratio between the sum value calculated for the anatomical layer and a sum of all the data elements that are in the at least two of the detected anatomical layers and in the subset of the OCT data; and
generating, as the supplementary image data, and based on an ordered sequence of the calculated ratios, wherein the calculated ratios are arranged in order of the corresponding anatomical layers of the eye, colour information defining a colour which is to be displayed in the combined image and identifies the ordered sequence of the calculated ratios, such that the colour is indicative of the variation, along the depth direction of the retina, of the measured reflectance of the eye in the selected subset of the OCT data.

10. The computer-implemented method according to claim 9, wherein
three anatomical layers in the selected subset of the OCT data are detected, and
the colour information is generated by assigning, to each of a red colour component, a green colour component and a blue colour component of the colour to be displayed in the combined image, a respective weighting for the colour component in accordance with a respective one of the calculated ratios in the ordered sequence of the calculated ratios.

11. The computer-implemented method according to claim 1, wherein the selected subset of the OCT data is processed to generate the supplementary image data by:
detecting a plurality of anatomical layers of the eye in the selected subset of the OCT data, the anatomical layers comprising one or more retinal layers of the retina;
calculating, for each anatomical layer of the detected anatomical layers, a respective sum value by summing values of data elements of the subset of the OCT data in the anatomical layer;
selecting, based on the calculated sum values, an anatomical layer of the detected anatomical layers which provides a dominant contribution to the measured reflectance of the eye; and
generating, as the supplementary image data, graphic image data defining a graphic which identifies the selected anatomical layer.

12. The computer-implemented method according to claim 1, wherein the selected subset of the OCT data represents a volumetric image of a part of the retina having a feature of a predetermined type and is processed to generate the supplementary image data by:
training a model for determining a depth of the feature of the predetermined type in the depth direction of the retina, by supervised learning of examples of OCT data of pathological regions of at least one other retina, each of the examples of OCT data comprising a single OCT A-scan or two or more adjacent OCT A-scans, and each of the pathological regions having a respective feature of the predetermined type, wherein an indication of a respective depth of the respective feature in the depth direction of the retina in each of the examples of OCT data is specified by a user during the training;
processing the selected subset of the OCT data using the trained model to determine the depth of the feature in the depth direction of the retina; and
generating, as the supplementary image data, one of
graphic image data defining a graphic which indicates the determined depth of the feature and is to be overlaid on the fundus image so as to indicate a location of the feature in the combined image, and
colour information defining a colour which is to be displayed at a location of the feature in the combined image and indicates the determined depth of the feature.

13. A non-transitory computer-readable storage medium storing a computer program comprising computer program instructions which, when executed by a computer processor, cause the computer processor to perform a method of processing image data defining a fundus image of a portion of a retina of an eye to include supplementary information on a designated feature in the fundus image, the method comprising:
designating a feature in the fundus image;
receiving optical coherence tomography, OCT, data of a C-scan of the portion of the retina;
selecting a subset of the OCT data which represents a volumetric image of a part of the retina at a location on the retina corresponding to a location of the designated feature in the fundus image;

processing the selected subset of the OCT data to generate, as the supplementary information, supplementary image data indicative of a variation, along a depth direction of the retina, of a measured reflectance of the eye in the selected subset of the OCT data; and generating combined image data by combining the image data with the supplementary image data, such that a combined image defined by the combined image data provides an indication of the variation at the designated feature.

14. An apparatus for processing image data defining a fundus image of a portion of a retina of an eye to include supplementary information on a designated feature in the fundus image, the apparatus comprising:

a feature designation module arranged to designate a feature in the fundus image;

a receiver module arranged to receive optical coherence tomography, OCT, data of a C-scan of the portion of the retina;

a selection module arranged to select a subset of the OCT data which represents a volumetric image of a part of the retina at a location on the retina corresponding to a location of the designated feature in the fundus image;

a supplementary image data generation module arranged to process the selected subset of the OCT data to generate, as the supplementary information, supplementary image data indicative of a variation, along a depth direction of the retina, of a measured reflectance of the eye in the selected subset of the OCT data; and a combined image data generation module arranged to generate combined image data by combining the image data with the supplementary image data, such that a combined image defined by the combined image data provides an indication of the variation at the designated feature.

* * * * *